United States Patent
Metzger et al.

(10) Patent No.: US 10,463,630 B2
(45) Date of Patent: Nov. 5, 2019

(54) INTERACTION OF METHYLATED LSD1 AND CHD1, A COMPOUND INHIBITING THIS INTERACTION FOR USE IN THERAPY, AND A SCREENING METHOD FOR SUCH A COMPOUND

(71) Applicant: Albert-Ludwigs-Universität Freiburg, Freiburg (DE)

(72) Inventors: Eric Metzger, Neuf-Brisach (FR); Roland Schüle, Weisweil (DE)

(73) Assignee: Albert-Ludwigs-Universität Freiurg, Freiburg (DE)

( * ) Notice: Subject to any disclaimer, the term of this patent is extended or adjusted under 35 U.S.C. 154(b) by 96 days.

(21) Appl. No.: 15/554,169

(22) PCT Filed: Feb. 24, 2016

(86) PCT No.: PCT/EP2016/053808
§ 371 (c)(1),
(2) Date: Aug. 28, 2017

(87) PCT Pub. No.: WO2016/135165
PCT Pub. Date: Sep. 1, 2016

(65) Prior Publication Data
US 2018/0036256 A1 Feb. 8, 2018

(30) Foreign Application Priority Data

Feb. 27, 2015 (GB) .................................. 1503339.2

(51) Int. Cl.
*A61K 31/00* (2006.01)
*G01N 33/68* (2006.01)
(52) U.S. Cl.
CPC ......... *A61K 31/00* (2013.01); *G01N 33/6845* (2013.01); *G01N 2333/902* (2013.01); *G01N 2333/90245* (2013.01); *G01N 2333/914* (2013.01); *G01N 2440/12* (2013.01); *G01N 2500/02* (2013.01)

(58) Field of Classification Search
CPC .......................... A61K 31/00; G01N 33/6845
See application file for complete search history.

(56) References Cited

PUBLICATIONS

Burkhard et al., "CHD1 is a 5q21 Tumor Suppressor Required for ERG Rearrangement in Prostate Cancer," *Cancer Research*, 73(9): 2795-2805 (May 1, 2013).
He et al., "Targeting protein lysine methylation and demethylation in cancers," *Acta Biochim Biophys Sin*, 44(1): 70-79 (Dec. 22, 2011).
Metzger et al., "Assembly of methylated KDM1A and CHD1 drives androgen receptor—dependent transcription and translocation," *Nature, Structural and Molecular Biology*, 23(2): 132-139 (Feb. 1, 2016).
Metzger et al., "LSD1 demethylates repressive histone marks to promote androgen-receptor-dependent transcription," *Nature*, 437(7057): 1-4 (Sep. 15, 2005).
European Patent Office, International Search Report in International Patent Application No. PCT/EP2016/053808, dated Apr. 4, 2016, 7 pp.
European Patent Office, Written Opinion in International Patent Application No. PCT/EP2016/053808, dated Apr. 4, 2016, 8 pp.

*Primary Examiner* — Gyan Chandra
(74) *Attorney, Agent, or Firm* — Leydig, Voit & Mayer, Ltd.

(57) ABSTRACT

Disclosed in the present application are: (i) a compound inhibiting the interaction between LSD1me2 and CHD1 for use in therapy, (ii) a compound inhibiting the interaction between LSD1me2 and CHD1 for use in treating cancer, in particular prostate cancer, and (iii) a method of screening for such a compound.

5 Claims, 19 Drawing Sheets
(9 of 19 Drawing Sheet(s) Filed in Color)
Specification includes a Sequence Listing.

a b c d e a b

LSD1 / CHD1 co-crystal structure c f c d

— LSD1 K114me2 (-DHT)
— LSD1 K114me2 (+DHT)

— CHD1 (-DHT)
— CHD1 (+DHT)

g h

LNCaP cells / TMPRSS2 enhancer (-13782/-13866)

i a

CHD1 / LSD1 K114me2 interaction b

CHD1 / H3K4me3 interaction c

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
gccacctggt gaagtgcaga                                                20

<210> SEQ ID NO 2
<211> LENGTH: 20
<212> TYPE: DNA
<213> ORGANISM: Artificial Sequence
<220> FEATURE:
<223> OTHER INFORMATION: Primer Sequence

<400> SEQUENCE: 2
tggagctagt gctgcatgtc                                                20

<210> SEQ ID NO 3
<211> LENGTH: 23
<212> TYPE: DNA
<213> ORGANISM: Artificial Sequence
<220> FEATURE:
<223> OTHER INFORMATION: Primer Sequence

<400> SEQUENCE: 3
ttatctagga cagtaagcaa gcc                                            23

<210> SEQ ID NO 4
<211> LENGTH: 21
<212> TYPE: DNA
<213> ORGANISM: Artificial Sequence
<220> FEATURE:
<223> OTHER INFORMATION: Primer Sequence

<400> SEQUENCE: 4
ggatgtttgt aaagcaggca t                                              21

<210> SEQ ID NO 5
<211> LENGTH: 24
<212> TYPE: DNA
<213> ORGANISM: Artificial Sequence
<220> FEATURE:
<223> OTHER INFORMATION: Primer Sequence

<400> SEQUENCE: 5
tcctaatgac atttgatgtt cagc                                           24

<210> SEQ ID NO 6
<211> LENGTH: 22
<212> TYPE: DNA
<213> ORGANISM: Artificial Sequence
```

```
<220> FEATURE:
<223> OTHER INFORMATION: Primer Sequence

<400> SEQUENCE: 6
cccttaaaag tcaacaacaa ga                                              22

<210> SEQ ID NO 7
<211> LENGTH: 20
<212> TYPE: DNA
<213> ORGANISM: Artificial Sequence
<220> FEATURE:
<223> OTHER INFORMATION: Primer Sequence

<400> SEQUENCE: 7
aactgccaaa gctggatctg                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer Sequence

<400> SEQUENCE: 8
ccaggtagct gggttacagg                                                 20

<210> SEQ ID NO 9
<211> LENGTH: 24
<212> TYPE: DNA
<213> ORGANISM: Artificial Sequence
<220> FEATURE:
<223> OTHER INFORMATION: Primer Sequence

<400> SEQUENCE: 9
gagccatgaa agtctttgct atga                                            24

<210> SEQ ID NO 10
<211> LENGTH: 20
<212> TYPE: DNA
<213> ORGANISM: Artificial Sequence
<220> FEATURE:
<223> OTHER INFORMATION: Primer Sequence

<400> SEQUENCE: 10
aagttcacac cttcctgggt                                                 20

<210> SEQ ID NO 11
<211> LENGTH: 23
<212> TYPE: DNA
<213> ORGANISM: Artificial Sequence
<220> FEATURE:
<223> OTHER INFORMATION: Primer Sequence

<400> SEQUENCE: 11
gtgatccttc ccacctgtac att                                             23

<210> SEQ ID NO 12
<211> LENGTH: 20
<212> TYPE: DNA
<213> ORGANISM: Artificial Sequence
<220> FEATURE:
<223> OTHER INFORMATION: Primer Sequence

<400> SEQUENCE: 12
aggacacagg aaagcgatgg                                                 20
```

```
<210> SEQ ID NO 13
<211> LENGTH: 20
<212> TYPE: DNA
<213> ORGANISM: Artificial Sequence
<220> FEATURE:
<223> OTHER INFORMATION: Primer Sequence

<400> SEQUENCE: 13
agagggctgt cttgattcgc                                                20
```

INTERACTION OF METHYLATED LSD1 AND CHD1, A COMPOUND INHIBITING THIS INTERACTION FOR USE IN THERAPY, AND A SCREENING METHOD FOR SUCH A COMPOUND

CROSS-REFERENCE TO RELATED APPLICATIONS

This patent application is the U.S. national phase of International Patent Application No. PCT/EP2016/053808, filed on Feb. 24, 2016, which claims the benefit of United Kingdom Patent Application No. 1503339.2, filed Feb. 27, 2015, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 2,844 byte ASCII (Text) file named "Corrected_730702_ST25.txt," created Jul. 12, 2018.

FIELD OF THE INVENTION

The present invention is concerned with a compound inhibiting the interaction between methylated lysine-specific demethylase 1 (LSD1) and chromodomain-helicase-DNA-binding protein 1 (CHD1) for use in therapy. The present invention further relates to such a compound for use in the treatment of cancer, in particular for use in the treatment of prostate cancer. The present invention is also concerned with a method of screening for such a compound.

BACKGROUND OF THE INVENTION

Prostate cancer is the most common type of cancer found in men and the second leading cause of cancer deaths in Western countries. Chromosomal rearrangements and extensive copy number alterations are prevalent in prostate cancer, whereas point mutations are relatively rare[6,7,8]. Chromosomal rearrangements occur in a coordinated fashion by a phenomenon termed chromoplexy[1]. Chromoplectic tumors are characterized by presence of the TMPRSS2-ERG gene fusion and expression of a functional chromatin-remodelling enzyme CHD1[1,2]. Recent data suggest that CHD1 is directly involved in TMPRSS-ERG fusion and that the chromosomal rearrangements resulting in the generation of TMPRSS-ERG fusion are coupled to androgen receptor (AR)-dependent transcription[9].

In recent years, LSD1 was identified as a potential target for prostate cancer therapy[10,11,12]. LSD1 is a histone demethylase that removes mono- and dimethyl marks from either lysine 4 or lysine 9 of histone 3 (H3)[10,13]. When associated with AR, the enzyme removes repressive methyl marks from H3K9, thereby enhancing AR-dependent gene transcription and prostate tumor cell proliferation[10].

There is the need for compounds which block the AR-dependent gene transcription and can thus be used in prostate tumor therapy. It is of course highly desirable that these compounds are as selective as possible in order not to interfere with further signal transduction pathways in the cells. Screening methods for such compounds are of course also of high interest.

LSD1 is not only implicated in prostate cancer but also in carcinogenesis and in maintenance of the malignant state in various other cancers. Thus, besides prostate cancer, a role for LSD1 has also been described breast cancer (see e.g. Lim et al., *Carcinogenesis*. 2010 March; 31(3): 512-20), colon cancer (see e.g. Huang et al., *Clin Cancer Res.* 2009; 15:7217-7228) and neuroblastoma (see e.g. Schulte et al., *Cancer Res.* 2009 Mar. 1; 69(5): 2065-71). Further, overexpression of LSD1 has been implicated in carcinogenesis of bladder, lung and colorectal cancer (see e.g. Hayami et al., *Int J Cancer.* 2011 Feb. 1; 128(3): 574-86) and a role for LSD1 in the self-renewal of leukemic stem cells in acute myeloid leukemia (AML) has been described (see e.g. Mould et al., *Med Res Rev* 2014 Nov. 24 doi: 10.1002/med.21334, wherein inhibitors of LSD1 for the treatment of AML are also disclosed).

There is of course also an ongoing need for novel compounds for use in therapy of these cancer types. Again, it is highly desirable that these compounds are as selective as possible in order not to interfere with further signal transduction pathways in the cells. Screening methods for such compounds to be used in the therapy of other cancer types are of course also of high interest.

OBJECTS AND SUMMARY OF THE INVENTION

The inventors of the present invention inter alia surprisingly found that LSD1 is methylated and that this methylation serves as regulatory switch to allow for interaction with CHD1. This interaction triggers the binding of the AR to chromatin and thus drives and increases the expression of androgen-dependent genes. Further, androgen-dependent chromosomal rearrangement such as the TMPRSS2-ERG oncogenic fusion during prostate tumor evolution are induced by this interaction. Prostate cancer treatment inter alia aims at decreasing or blocking the expression of androgen-dependent genes as well as androgen-dependent chromosomal rearrangement, and a compound inhibiting the interaction between methylated LSD1 and CHD1 may thus be used in cancer therapy to downregulate or block hormone-dependent gene expression, in particular in prostate cancer therapy.

In a first aspect, the present invention thus relates to a compound inhibiting the interaction between LSD1me2 and CHD1 for use in therapy.

In an embodiment, said compound specifically inhibits the interaction between LSD1me2 and CHD1. In another embodiment thereof, said compound inhibits only the interaction between LSD1me2 and CHD1.

In a preferred embodiment, said compound inhibits the interaction between (i) LSD1me2 and (ii) an acidic surface bridging chromodomain 1 and chromodomain 2 of CHD1 and amino acids of chromodomain 1 and chromodomain 2 of CHD1.

In another preferred embodiment, said compound inhibits at least one interaction between amino acids T110, S111, R112, R113, K144me2, R115 and A116 of LSD1me2 and amino acids Y295, W322, W325, D408 and D425 of CHD1. It is noted that Y295, W322 and W325 are comprised in the chromodomain 1 of CHD1, whereas D408 and D425 are comprised in the chromodomain 2 of CHD1.

In an even preferred embodiment, said compound inhibits at least one interaction selected from the group consisting of the interaction between amino acid S111 of LSD1me2 and D408 of CHD1, the interaction between amino acid R112 of LSD1me2 and W325 of CHD1, the interaction between amino acid R113 of LSD1me2 and D425 of CHD1, the interaction between the backbone between amino acids R113 and K114me2 of LSD1me2 and Y295 of CHD1, and the interaction between amino acid K114me2 of LSD1me2 and W322 of CHD1.

In a most preferred embodiment, said compound inhibits the interaction between R113 of LSD1me2 and D425 of CHD1. This is preferably understood herein as referring to an inhibition of the interaction between R113 of LSD1me2 and D425 of CHD1 only. It is noted that said interaction between R113 of LSD1me2 and D425 of CHD1 is bridged by a water molecule. It is further noted that D425 of CHD1 binds to R113 of LSD1me2 (bridged via a water molecule) but apparently not to other CHD1-interacting proteins, such as e.g. H3K4me3. Accordingly, an inhibition of this interaction is most preferred since such a compound will specifically inhibit CHD1 binding to LSD1me2 but not the interaction of CHD1 e.g. with H3K4me3.

In another preferred embodiment, said compound fails to affect the interaction between CHD1 and H3K4me3. It is noted that the interaction between CHD1 and H3K4me3 is mediated by at least amino acids A1, R2, K4me3, and the backbone between amino acid T3 and K4me3 of H3K4me3, and amino acids Y295, W322, G324 and D408 of CHD1.

In one embodiment, said compound is the sole pharmaceutically active agent used in therapy. In another embodiment, an additional pharmaceutically active agent is used in therapy.

In a second aspect, the present invention relates to a compound for use as defined in the first aspect for use in a specific medical use, namely for use in treating cancer.

In a preferred embodiment of said second aspect, said cancer is selected from the group consisting of prostate cancer, breast cancer, colon cancer, neuroblastoma, bladder, lung, colorectal cancer and acute myeloid leukemia. In another preferred embodiment, said cancer is selected from prostate cancer, breast cancer and lung cancer. In another preferred embodiment, said cancer is selected from a hormone-dependent cancer, wherein it can be preferred that said hormone-dependent cancer is selected from prostate cancer and breast cancer.

In the most preferred embodiment, said cancer is prostate cancer. It can further be particularly preferred that said cancer is hormone-dependent prostate cancer.

The two aspects discussed above relate to a medical use of said compound and said compound may thus be present in a pharmaceutical composition. In a preferred embodiment, said composition is selected from the group consisting of an oral, buccal, nasal, rectal, topical, transdermal and parenteral composition.

In a third aspect, the present invention relates to a method of screening for a compound as defined above.

Said method of screening for a compound inhibiting the interaction between LSD1me2 and CHD1 comprises the steps of:
1) Contacting a compound with CHD1 or a fragment thereof;
2) Determining whether said compound binds to CHD1 or a fragment thereof at the binding site for LSD1me2;

wherein a compound inhibiting the interaction between LSD1me2 and CHD1 binds to CHD1 at the binding site for LSD1me2.

In an embodiment thereof, said fragment of CHD1 comprises chromodomain 1 and chromodomain 2 of CHD1. Thus, said fragment of CHD1 may be comprised of amino acids 268 to 443 of CHD1 or amino acids 270 to 443 of CHD1. Preferably, said fragment consists of amino acids 268 to 443 or 270 to 443 of CHD1, wherein said fragment may further comprise a purification-tag, such as FLAG or GST.

In another preferred embodiment, CHD1 is recombinant CHD1. Accordingly, a fragment thereof is then a recombinant fragment thereof.

In another preferred embodiment, said binding site for LSD1me2 in CHD1 is an acidic surface bridging chromodomain 1 and chromodomain 2 of CHD1 and further comprised of amino acids of chromodomain 1 and chromodomain 2 of CHD1.

In a preferred embodiment, said binding site for LSD1me2 in CHD1 is defined by amino acids Y295, W322, W325 from chromodomain 1 and D408 and D425 from chromodomain 2 of CHD1. This does not exclude that at least one further amino acid and/or the protein backbone of CHD1 also interacts with LSD1me2.

In the most preferred embodiment, said binding site for LSD1me2 in CHD1 is defined by amino acid D425 of CHD1. Since this amino acid in CHD1 binds to LSD1me2 (more specifically to R113 of LSD1me2 bridged via a water molecule) but apparently not to other CHD1-interacting proteins, such as e.g. H3K4me3, binding of the compound to this binding site is most preferred since such a compound will specifically only inhibit CHD1 binding to LSD1me2.

In another embodiment, said determining step 2) is carried out by a method selected from the group consisting of nuclear magnetic resonance spectroscopy, mass spectrometry, infrared spectroscopy, Raman spectroscopy, electron microscopy and X-ray crystallography. It can be preferred to use nuclear magnetic resonance or X-ray crystallography, wherein X-ray crystallography is most preferred.

In a preferred embodiment, said method comprises the following steps:
1) Contacting a compound with CHD1 or a fragment thereof;
2) Determining whether said compound binds to CHD1 or a fragment thereof;
3) Determining whether said compound binds to CHD1 or a fragment thereof at the binding site for LSD1me2;
4) Optionally modifying the structure of said compound to increase binding affinity and/or specificity to the binding site for LSD1me2;

wherein a compound inhibiting the interaction between LSD1me2 and CHD1 (i) binds to CHD1 in step 2) and (ii) binds to CHD1 at the binding site for LSD1me2 in step 3).

The embodiments defined above for specific steps also apply to the method comprising additional steps, wherein the new numbering of the steps is then of course to be taken into account for these embodiments. The additional step 2) may facilitate the method of screening since a compound may initially be excluded if it fails to bind to CHD1. In a preferred embodiment, step 2) is reiterated with the compound initially identified in step 2) as binding to CHD1 or a fragment thereof.

Preferably, said step of determining in additional step 2) is carried out by a method selected from the group consisting of circular dichroism spectroscopy, differential scanning fluorimetry, nuclear magnetic resonance spectroscopy, isothermal titration calorimetry, surface plasmon resonance, and fluorescence polarization.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
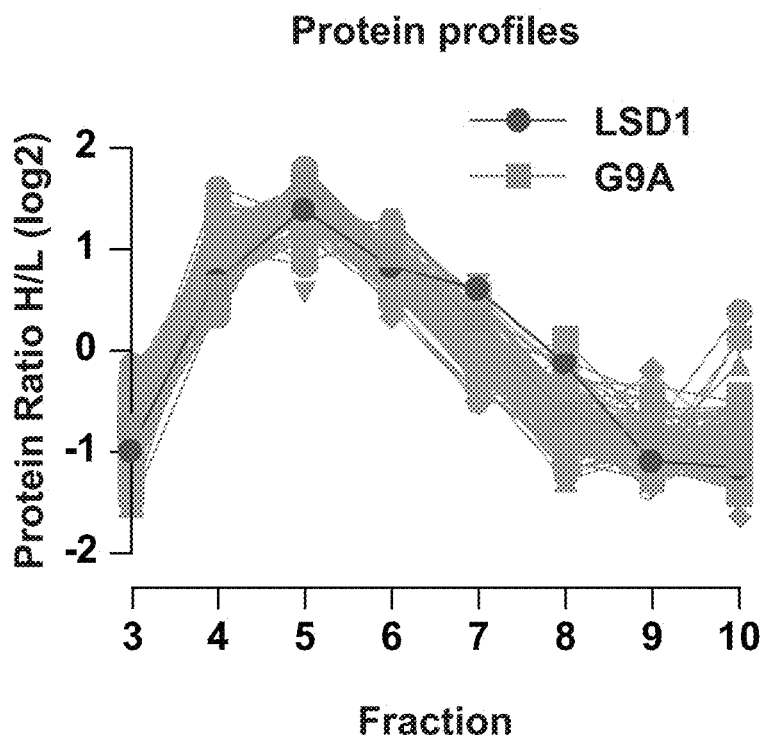
FIG. 1: LSD1 is methylated at K114. (a) Protein enrichment profiles of a cluster of 166 proteins obtained from PCP-SILAC in LNCaP cells. Enrichment profiles of LSD1 and G9A are represented in color lines. (b) Extracts from 293T cells transfected with Flag-LSD1 or Flag-LSD1 K114A in the presence or absence of Flag-G9A were immunoprecipitated with anti-Flag antibody and analyzed by Western blot. (c) Recombinantly expressed, purified GST-LSD1 or GST-LSD1 K114A was incubated in the presence or absence of purified GST-G9A aa786-1210 with or without S-adenosyl-methionine (SAM). (d,e) Levels of LSD1 K114me2 were analyzed in different cell types. (b-e) Western blots were decorated with the indicated antibodies.
Figure 1:
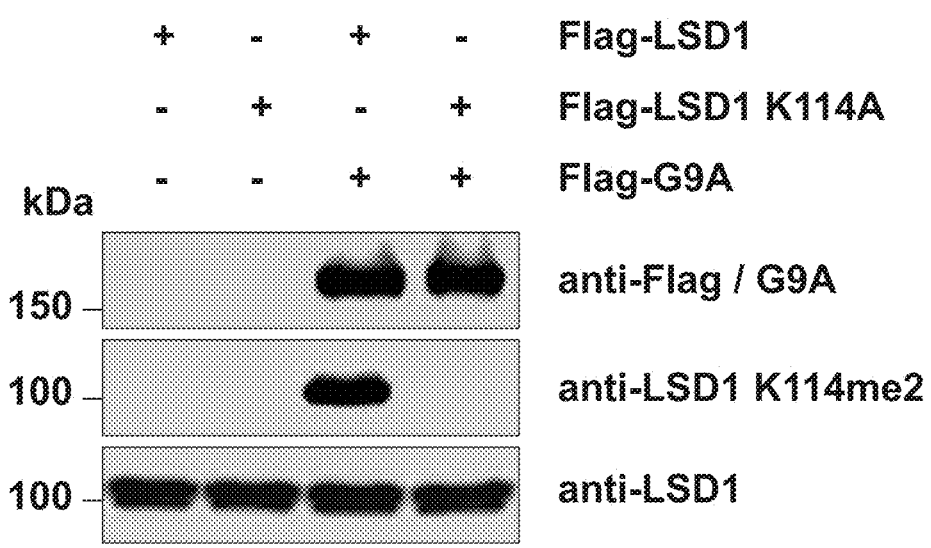
Figure 1:
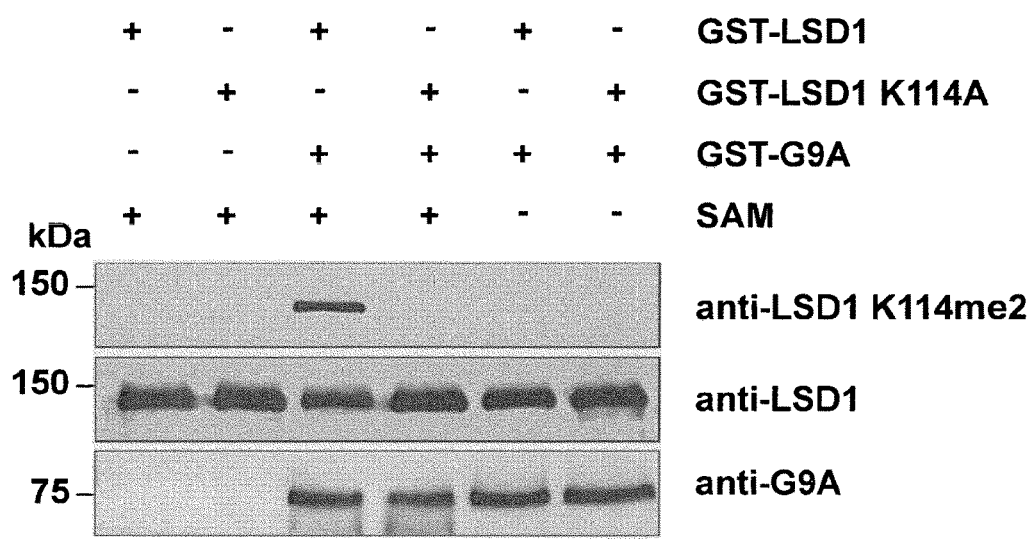
Figure 1:
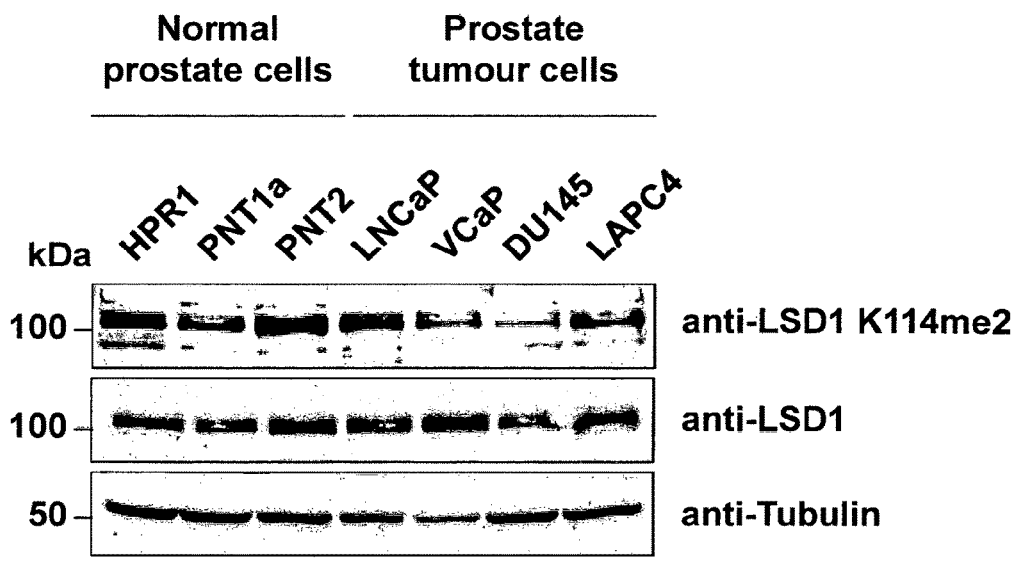
Figure 1:
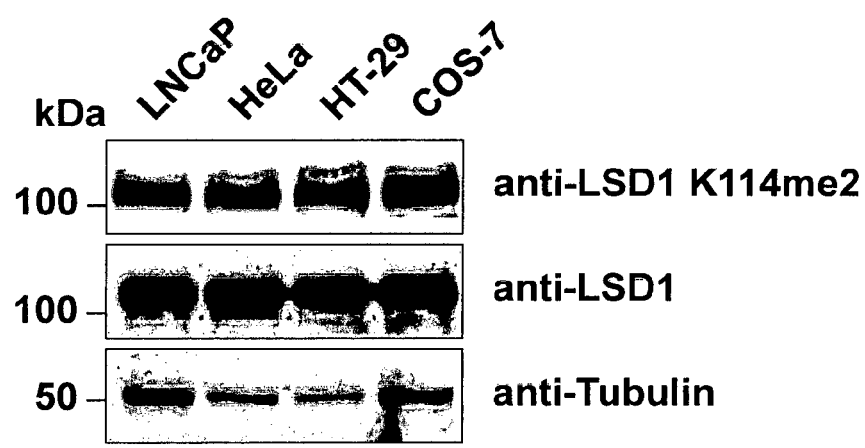

The inventors of the present invention inter alia succeeded in unraveling a novel mechanism that is not only crucial for regulating androgen-dependent gene expression but also controls androgen-dependent chromosomal rearrangement such as the TMPRSS2-ERG oncogenic fusion.

This mechanism may be referred to as the androgen-regulated G9A/LSD1 K114me2/CHD1 circuit and compounds inhibiting the interaction between LSD1 K114me2 and CHD1 may be used to downregulate or block downstream events of the LSD1 K114me-CHD1-interaction, such as e.g. the downregulation or blocking of androgen-dependent gene expression in prostate cancer.

1. Definitions and Description of the Underlying Mechanism

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "LSD1" as used herein refers to the enzyme "lysine-specific demethylase 1" with the UniProt accession number O60341 comprising 852 amino acids.

The term "LSD1me2" is interchangeable used herein with the term "LSD1 K114me2" and refers to LSD1 that is modified at lysine residue 114 by two methyl-groups. Reference to a "methylation of LSD1" also refers to this post-translational modification of LSD1.

In general, the indication of "me" after the amino acid "K" (i.e. lysine) indicates that the corresponding lysine residue is methylated. The number, e.g. "2" indicates that there are two methyl-groups present at the corresponding lysine, e.g. "K114me2". Another example is "K4me3", where three methyl-groups are present at lysine 4.

The term "CHD1" as used herein refers to the enzyme "chromodomain-helicase-DNA-binding protein 1" with the UniProt accession number O14646 comprising 1710 amino acids. CHD1 comprises two chromodomains, namely chromodomain 1 comprising amino acids 268 to 356 and chromodomain 2 comprising amino acids 389 to 443 of CHD1. The term "chromodomain" as used herein refers to a protein structural domain of about 40 to 50 amino acids commonly found in proteins associated with the remodeling and manipulation of chromatin. Chromodomain-containing proteins are responsible for aspects of gene regulation related to chromatin remodeling and formation of heterochromatin regions. Chromodomain-containing proteins bind methylated histones.

The term "H3K4me3" as used herein refers to histone 3 (H3) that is modified at lysine residue 4 by three methyl-groups.

The term "compound" as used herein refers to an organic compounds, preferably a small organic compound having a low molecular weight (also termed "small molecule" in the respective field). The compound may be a synthetic compound not known to occur in nature or a naturally-occurring compound isolated from or known to occur in natural sources, such as e.g. plants, fungi or the like. Before the background of the present invention, it is important to note that the main focus is on a compound that is capable of inhibiting the interaction between LSD1me2 and CHD1, and that such compounds may e.g. be identified in the method of screening disclosed herein. When reference is made herein to a "compound" within the context of such a method, the term compound may also refer to a "small chemical fragment". This term is typically used in the field of drug discovery and relates to the starting pool of molecules during the process of drug discovery ("fragment-based lead discovery"), wherein a small chemical fragment that has been identified as promising binding partner may undergo structural modifications to increase the binding affinity and/or specificity.

The term "inhibiting the interaction" as used herein means that preferably no interaction at all (at least not to a detectable level) between two proteins/relevant fragments thereof takes place any more. However, when a given interaction between two proteins (set to 100%) is greatly reduced, e.g. to a level of about 70%, about 60%, about 50%, about 40%, about 30%, preferably about 20%, more preferably about 10% or most preferably about 5% or less, such a reduced interaction is still encompassed by the term "inhibiting the interaction". In terms of the medical use of compound inhibiting an interaction, a complete inhibition of an interaction may not be required to achieve a sufficient therapeutic effect. Thus, it needs to be understood that the term "inhibiting" as used herein also refers to a reduction of an interaction, which is sufficient to achieve the desired effect.

The term "specifically inhibiting" as used herein means that the inhibition abolishes or reduces only the interaction between protein A and protein B, in the present case between LSD1me2 and CHD1, without e.g. affecting further interactions of LSD1me2 with other proteins and/or of CHD1 with other proteins. This may also be referred to as "inhibiting only" a given interaction. The effect of such a "specific inhibition" is that only the desired downstream effect is affected (in the present case abolished or reduced), whereas other downstream effects mediated via different interactions still take place. Importantly, as outlined below in the example section in more detail, the inhibition according to the present invention is preferably specific for the interaction between LSD1me2 and CHD1 and preferably fails to have an effect on the interaction between CHD1 and H3K4me3.

The present inventors could show that methylation of LSD1 is executed by G9A in an androgen-dependent manner and serves as a regulatory switch to allow for an interaction with CHD1. The androgen-regulated G9A/LSD1 K114me2/CHD1 circuit controls chromatin binding of AR. Accordingly, the mechanism is not only crucial for regulating androgen-dependent gene expression but also controls androgen-dependent chromosomal rearrangement such as the TMPRSS2-ERG oncogenic fusion during prostate tumor evolution.

Figure 5:
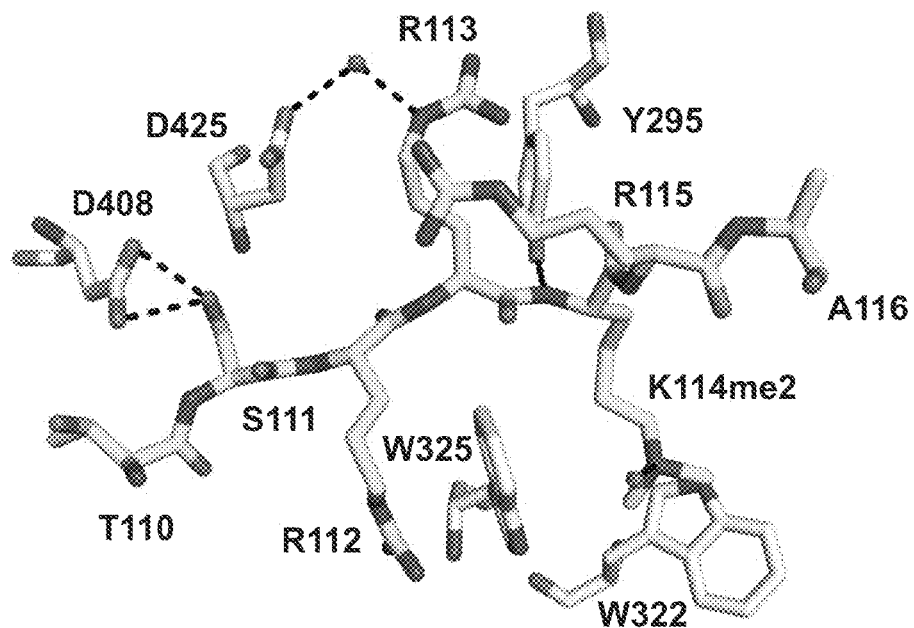
FIG. 5: CHD1 interacts with LSD1 K114me2. (a,b) View of the intermolecular interactions between the bound LSD1 peptide in yellow (a) and H3 peptide in cyan (b) with CHD1 residues (shown in the same orientation in gray), with hydrogen bonds shown as dashed lines. (c) Superimposition of LSD1aa110-116 K114me2 and H3aa1-5 K4me3 in complex with CHD1aa270-443. CHD1aa-270-443 is shown as a gray surface representation. LSD1 and H3 peptides are shown as stick models in yellow and cyan, respectively. The binding surface in CHD1 for inhibitors specifically interfering with LSD1 K114me2 but not H3K4me3 binding is shown in red.
Figure 5:
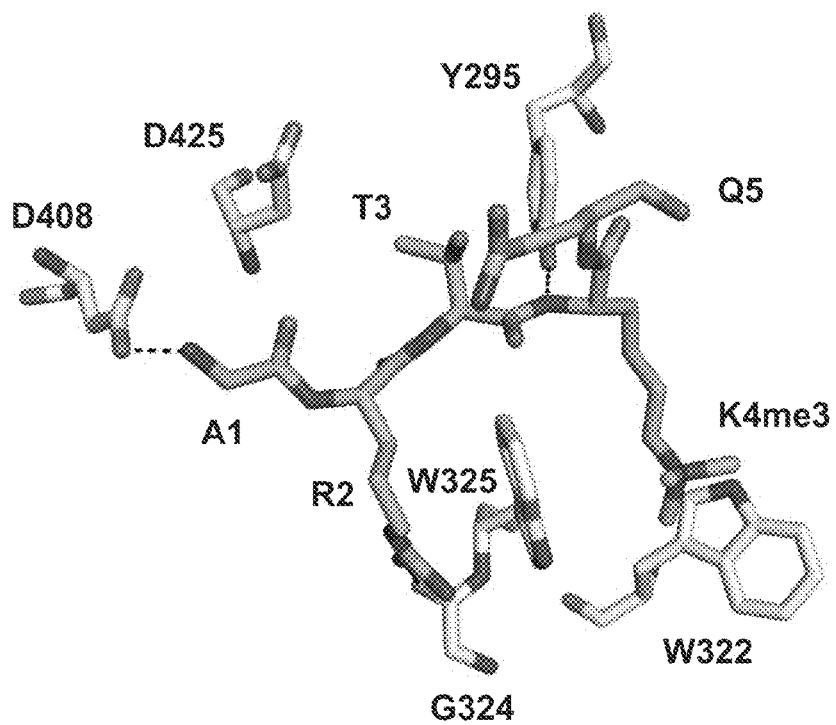
Figure 5:
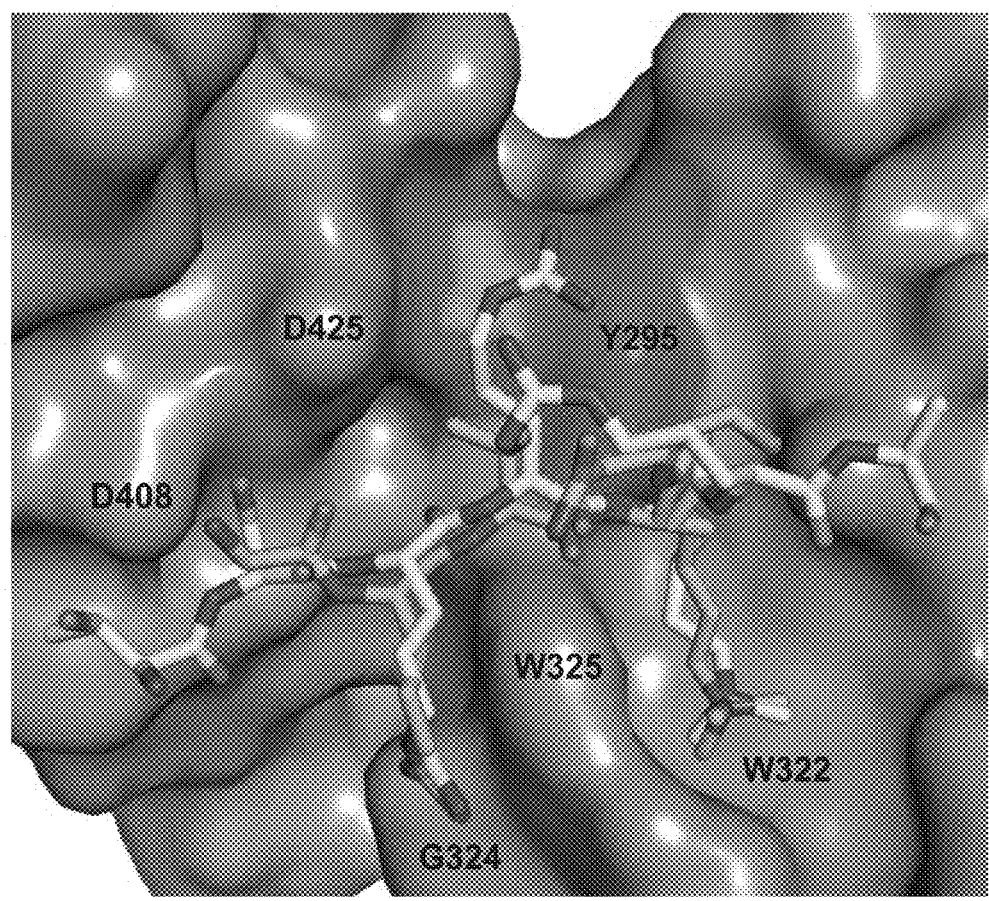

It can be derived inter alia from a superimposition of the crystal structures of CHD1/LSD1 K114me2 and CHD1/H3K4me3 that there is a significant difference in the binding modalities (see FIG. 5). This strongly suggests the potential to selectively target the CHD1/LSD1 K114me2 interface without affecting binding of CHD1 to H3K4me3. Accordingly, the binding of CHD1 to H3K4me3 would not be altered, with the result that CHD1 would still be capable of fulfilling its functions mediated via H3K4me3, which are not involved in prostate cancer tumor progression.

Thus, the examples of the present application, in particular examples 2 and 4 revealing the structures and employing specific mutants of either LSD1 and CH1 to study interactions and complex formations, clearly suggest that compounds targeting the CHD1/LSD1 K114me2 interaction represent inhibitors of in particular the AR functions for the treatment of cancer, particularly prostate cancer.

2. Pharmaceutical Composition of the Compound of the Present Invention

The term "for use in therapy" is used herein in the meaning that the compound is comprised in a "pharmaceutical composition", i.e. in the meaning of a first medical indication.

"Pharmaceutically active agent" as used herein means that a compound is potent of modulating a response in a human or animal being in vivo. The term "pharmaceutically acceptable excipient" as used herein refers to compounds commonly comprised in pharmaceutical compositions, which are known to the skilled person. Such compounds or excipients are exemplary listed below. In view of the definition "pharmaceutically active agent" as given above, a pharmaceutically acceptable excipient can be defined as being pharmaceutically inactive.

A pharmaceutical composition according to the present invention may be formulated for oral, buccal, nasal, rectal, topical, transdermal or parenteral application. Oral application can be preferred. Parenteral application can also be preferred and includes intravenous, intramuscular or subcutaneous administration. A pharmaceutical composition of the present invention may also be designated as formulation or dosage form.

In general, the dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, salt solutions, alcohols, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethyl-cellulose, polyvinylpyrrolidone and the like. The pharmaceutical compositions can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions in water-soluble form. Additionally, suspensions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a pharmaceutical composition of the present invention. Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluent or solvent. Among the acceptable vehicles and solvents that can be used are water and isotonic sodium chloride solution. Sterile oils are also conventionally used as solvent or suspending medium.

Suppositories for rectal administration of a pharmaceutical composition of the present invention can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the active agent from said suppositories.

For administration by inhalation, the pharmaceutical composition comprising a compound according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the active agent or a sustained release of the active agent.

As regards human patients, the compound of the present invention as comprised in a pharmaceutical composition may be administered to a patient in an amount of about 0.001 mg to about 1000 mg per day, preferably of about 0.01 mg to about 10 mg per day, more preferably of about 0.1 mg to about 5 mg per day.

As noted above, a pharmaceutical composition of the present invention may comprise the compound of the present invention as the only pharmaceutically active agent. Alternatively, said pharmaceutical composition may comprise at least one further independent pharmaceutically active agent in addition to said compound. As outlined above, the pharmaceutical composition according to the present invention may particularly be used in the treatment of cancer and the specific cancer types as outlined above, respectively, such that at least one further independent pharmaceutically active agent directed to the treatment of cancer and such cancer types (such as e.g. a chemotherapeutic agent) may be additionally present.

3. A Method of Screening of the Present Invention

As indicated above, the method of screening for a compound inhibiting the interaction between LSD1me2 and CHD1 comprises at least the steps of:
1) Contacting a compound with CHD1 or a fragment thereof;
2) Determining whether said compound binds to CHD1 or a fragment thereof at the binding site for LSD1me2;
wherein a compound inhibiting the interaction between LSD1me2 and CHD1 binds to CHD1 at the binding site for LSD1me2.

Said method may be carried out in the form of a virtual screening, which is known to the skilled person and which is carried out in accordance with standard and routine practice by the skilled person.

In a first virtual screening approach, a compound inhibiting the interaction between LSD1me2 and CHD1 may be screened for by i) designing a compound with a similar shape to amino acids T110 to A116 of LSD1me2; ii) contacting said compound with CHD1 by virtually superimposing the structure of said compound and the structure of CHD1 (or a fragment thereof, preferably amino acids 270 to 443 of CHD1); and iii) virtually determining whether said compound binds to CHD1 (or the above fragment thereof) at the binding site for LSD1me2. This approach may be referred to as the "ligand-based" virtual screening approach.

In a second virtual screening approach, a compound inhibiting the interaction between LSD1me2 and CHD1 may be screened for by i) contacting a compound with CHD1 by docking said compound into the LSD1me2 binding site; and ii) virtually determining whether said compound binds to CHD1 at the binding site for LSD2me2 by applying a scoring function to estimate the likelihood that the ligand will bind to the protein with high affinity, wherein a compound inhibiting the interaction between LSD1me2 and CHD1 binds to CHD1 at the binding site for LSD1me2 and has a relatively high scoring function. This approach may be referred to as the "structure-based" virtual screening approach.

Following the virtual screening, a compound that has been identified is then usually tested in in vitro test methods, such as e.g. established cell culture models, for efficacy as regards the desired effect. Cell culture models of particular relevance for the present invention are e.g. disclosed in example 3 below.

The above method may also be carried out by a fragment-based drug discovery method. This method is also standard knowledge for the skilled person in drug discovery, see e.g. Wikipedia entry for "fragment-based lead discovery." Accordingly, the "compound" referred to in the following is interchangeable with the term "small chemical fragment" or "chemical fragment".

The following method is preferred when carrying out the method by a fragment-based drug discovery method, wherein said method comprises at least the following steps:
1) Contacting a compound with CHD1 or a fragment thereof;
2) Determining whether said compound binds to CHD1 or a fragment thereof;
3) Determining whether said compound binds to CHD1 or a fragment thereof at the binding site for LSD1me2;
4) Optionally modifying the structure of said compound to increase binding affinity and/or specificity to the binding site for LSD1me2;
wherein a compound inhibiting the interaction between LSD1me2 and CHD1 (i) binds to CHD1 in step 2) and (ii) binds to CHD1 at the binding site for LSD1me2 in step 3).

The term "modifying" in step 4) as used herein means that specific substituents of the compound may be deleted, added, or substituted by different substituents.

In this method comprising four steps, it is preferred to use recombinant CHD1 comprising amino acids 260 to 443, i.e. the two chromodomains. Thus, in this preferred embodiment, said compound is contacted in step 1) with recombinant CHD1 comprising amino acids 260 to 443.

In step 2), it is determined whether said compounds binds to this fragment of CHD1, preferably by a method selected from the group consisting of circular dichroism spectroscopy, differential scanning fluorimetry, nuclear magnetic resonance spectroscopy, isothermal titration calorimetry (see also examples of the present invention, in particular example 6), surface plasmon resonance, and fluorescence polarization. It can be particularly preferred to use differential scanning fluorimetry in step 2). A binding affinity in the range of mM, preferably in the range of about 10 mM and more preferably in the range of 1 mM can be sufficient in this step 2) for the definition of a "binding" to CHD1. This step is introduced in the preferred embodiment to exclude compounds in an initial step that do not bind to CHD1 at all.

Step 2) may be reiterated with the compounds identified as binding to CHD1 in the initial step 2). This time, more stringent parameters may be used and/or a binding affinity lower than in the mM-range (e.g. in the µM- or even in the nM-range) may be regarded as defining a "binding" of these compounds to CHD1.

In step 3), it is then determined whether said compound binds to the recombinant fragment of CHD1 discussed above at the binding site for LSD1me2. This can be done in principle by any method selected from the group consisting of nuclear magnetic resonance spectroscopy, mass spectrometry, infrared spectroscopy, Raman spectroscopy, electron microscopy, X-ray crystallography, and combinations thereof. It is particularly preferred to use X-ray crystallography, wherein the structure of the CHD1-fragment is solved in combination with the compound. This may be done by methods routinely known to the skilled person, e.g. by co-crystallization or by soaking of said compound. Reference to examples 2 and 6 of the present invention is made as regards suitable parameters and the like when using X-ray crystallography.

Following the fragment-based screening method, a compound that has been identified is then usually tested in in vitro test methods, such as e.g. established cell culture models, for efficacy as regards the desired effect. Cell culture models of particular relevance for the present invention are e.g. disclosed in example 3 below.

All of the above-mentioned methods are carried out according to standard methods known to the skilled person. As explained in the method of screening above, the "target protein" is CHD1 or a fragment thereof, the "target site" is the binding site for LSD1me2, and the compound may be referred to as the "ligand".

Just by way of example, the method of differential scanning fluorimetry is discussed in more detail in the following. The underlying principle is as follows: Differential Scanning Fluorimetry (DSF) is a thermal denaturation assay that measures the thermal stability of a target protein and a subsequent increase in protein melting temperature upon binding of a ligand to the protein. The binding of low molecular weight ligands can increase the thermal stability of a protein, as described by Koshland in 1958 and Linderstrom-Lang and Schellman in 1959. The thermal stability change is measured by performing a thermal denaturation curve in the presence of a fluorescent dye, such as Sypro Orange. Sypro orange binds nonspecifically to hydrophobic surfaces, and water strongly quenches the fluorescence of Sypro Orange. When the protein unfolds, the exposed hydrophobic surfaces bind the dye, resulting in an increase in fluorescence. The stability curve and its midpoint value (melting temperature, $T_m$) are obtained by gradually increasing the temperature to unfold the protein and measuring the fluorescence at each point. Curves are measured for protein only and protein+ligand, and $\Delta T_m$ is calculated. A fluorescence-based thermal shift assay can be performed on instruments that combine sample temperature control and dye fluorescence detection, such as RT-PCR machines. The assay allows high-throughput screening of ligands to the target protein. A typical assay is carried out as follows:

Materials:

A fluorometer equipped with temperature control or similar instrumentation (RT-PCR machines); suitable fluorescent dye; a suitable assay plate, such as 96 well RT-PCR plate.

Compound Solutions:

Test ligands are prepared at a 50- to 100-fold concentrated solution, generally in the 10-100 mM range. For titration, a typical experimental protocol employs a set of 12 well, comprising 11 different concentrations of a test compound with a single negative control well.

Protein Solution:

Typically, target protein is diluted from a concentrated stock to a working concentration of ~0.5-5 µM protein with dye into a suitable assay buffer. The exact concentrations of protein and dye are defined by experimental assay development studies.

Centrifugation and Oil Dispense:

A brief centrifugation (~1000×g-force, 1 min) of the assay plate to mix compounds into the protein solution, 1-2 µl silicone oil to prevent the evaporation during heating is overlaid onto the solution, followed by an additional centrifugation step (~1000×g-force, 1 min).

Instrumental Set Up:

A typical temperature ramp rates range from 0.1-10° C./min but generally in the range of 1° C./min. The fluorescence in each well is measured at regular intervals, 0.2-1° C./image, over a temperature range spanning the typical protein unfolding temperatures of 25-95° C.

In the following, examples of embodiments of the present invention are outlined. However, said examples should not be construed as limiting the scope of the present invention.

4. Examples

4.1. Example 1: LSD1 is Methylated by G9A at K114 In Vitro and In Vivo

To unravel LSD1-associated mechanisms that might control androgen-dependent TMPRSS-ERG fusion, a global proteomics approach was initiated by performing protein correlation profiling (PCP) of human prostate tumor LNCaP cells that were stable isotope labelled by amino acid in cell culture (SILAC). Cluster analysis of the PCP-SILAC data revealed that LSD1 shares a similar protein enrichment profile with 165 proteins. Among these proteins, the histone methyltransferase G9A was identified (FIG. 1a). Inspection of the LSD1 protein sequence suggested a potential methylation site at lysine (K) 114. Subsequently, a rabbit polyclonal antibody specific for LSD1 K114me2 was developed according to standard methods. To test whether G9A methylates LSD1 at K114 either Flag-tagged LSD1 or a LSD1 protein containing a K114 to alanine (A) mutation (LSD1 K114A) in the presence or absence of G9A was expressed in 293T cells. Cell extracts were immunoprecipitated with an anti-Flag antibody and subjected to Western blot analysis using an antibody specific for LSD1 K114me2 (FIG. 1b). LSD1 but not LSD1 K114A is methylated in presence of G9A (FIG. 1b). In LNCaP cells, it was observed that approximately 6% of total LSD1 is dimethylated at K114 (data not shown). To provide evidence that methylation of LSD1 at K114 by G9A is direct, recombinantly expressed and purified GST-LSD1 or GST-LSD1 K114A was incubated with G9A in the presence or absence of the methyl donor S-adenosyl methionine (SAM). As expected, GST-LSD1 but not GST-LSD1 K114A is methylated at K114 by G9A in the presence of SAM (FIG. 1c). Finally, Western blot analyses indicated that LSD1 K114me2 is present in various cell lines including normal prostate and prostate tumor cells (FIG. 1d,e). Taken together, the data unravel that LSD1 is methylated by G9A at K114 both in vitro and in vivo.

4.2. Example 2: CHD1 is a LSD1 K114me2 Reader

Figure 2:
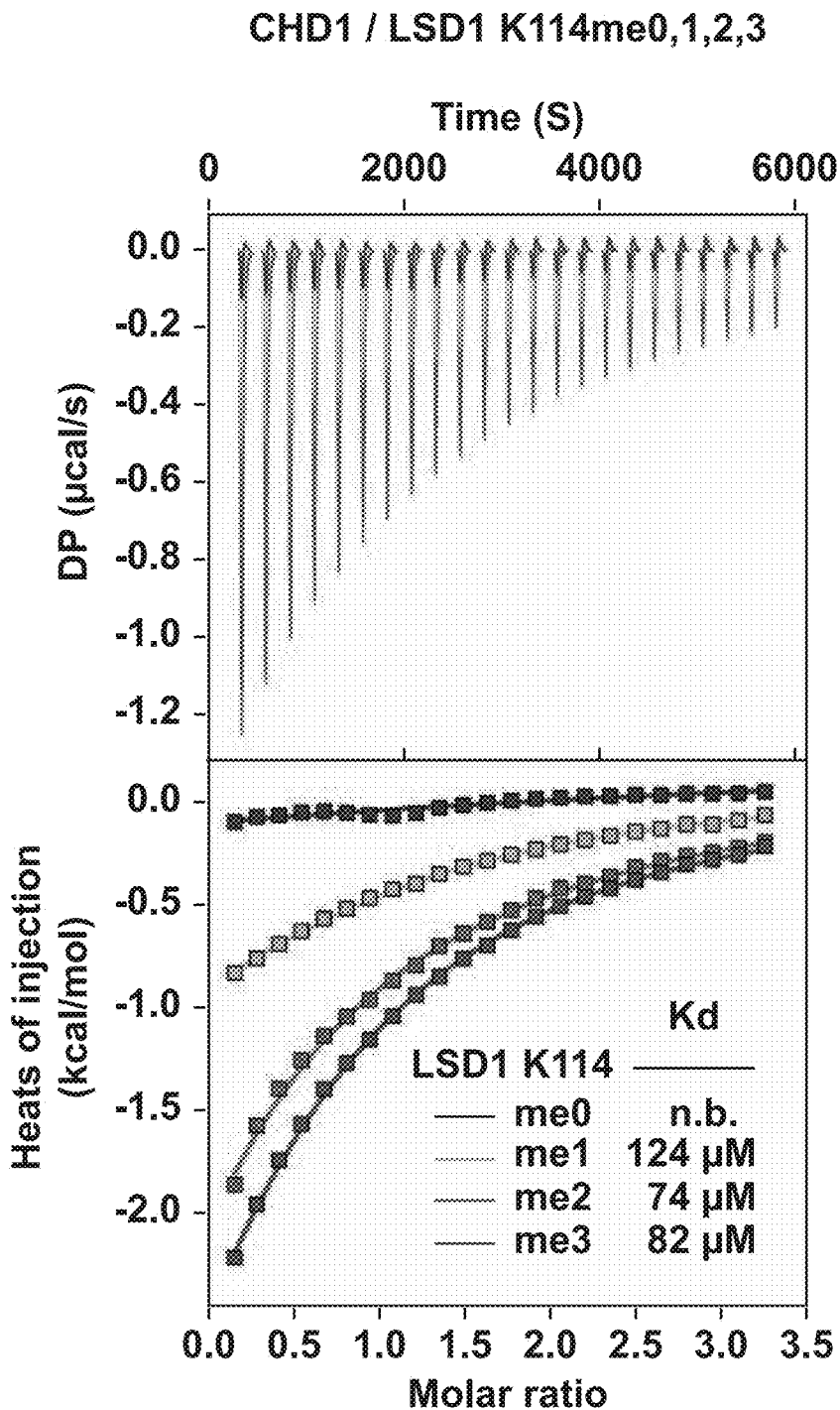
FIG. 2: CHD1 interacts with LSD1 K114me2. (a) Representative isothermal titration calorimetry (ITC) experiments displaying titration of LSD1aa104-127 K114me0, 1, 2, and 3 peptides to CHD1aa270-443. (b) Three-dimensional crystal structure of the CHD1aa270-443/LSD1aa110-116 K114me2 complex. CHD1 is shown as a gray surface representation and the LSD1 peptide as a stick model with C, O and N atoms colored yellow, red and blue, respectively. The location of the CHD1 residues forming the binding grooves for LSD1 K114me2 residues T110, S111, R113, K114me2, R115, and A116 is indicated with black labels. (c) View of a ($|F_o|-|F_c|$) omit map at 1.6 Å resolution contoured at 1σ as a blue mesh around LSD1 K114me2 peptide bound to CHD1. (d) Extracts from 293T cells transfected with Flag-LSD1 or Flag-LSD1 K114A in the absence or presence of G9A were immunoprecipitated with anti-Flag antibody. (e) LNCaP cell lysates were subjected to sucrose gradient centrifugation. Aliquots of the gradient fractions and total cell lysate (Input) were subjected to Western blot analysis. (f) Extracts from LNCaP cells were immunoprecipitated with anti-G9A antibody and subjected to Western blot analysis. Rabbit IgG (rIgG) was used as control. (d-f) Western blots were decorated with the indicated antibodies.
Figure 2:
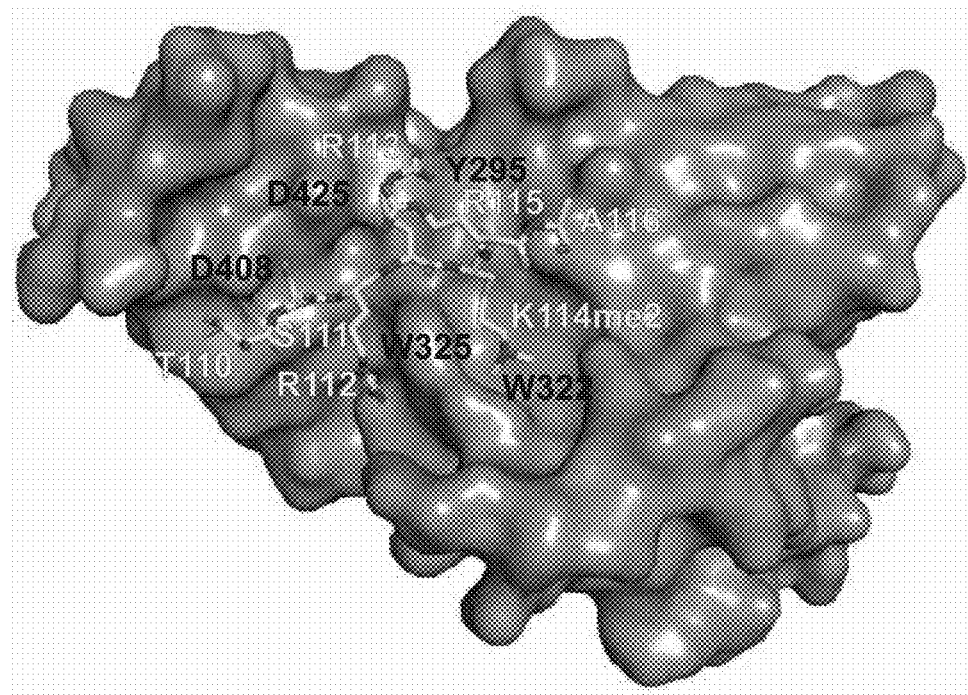
Figure 2:
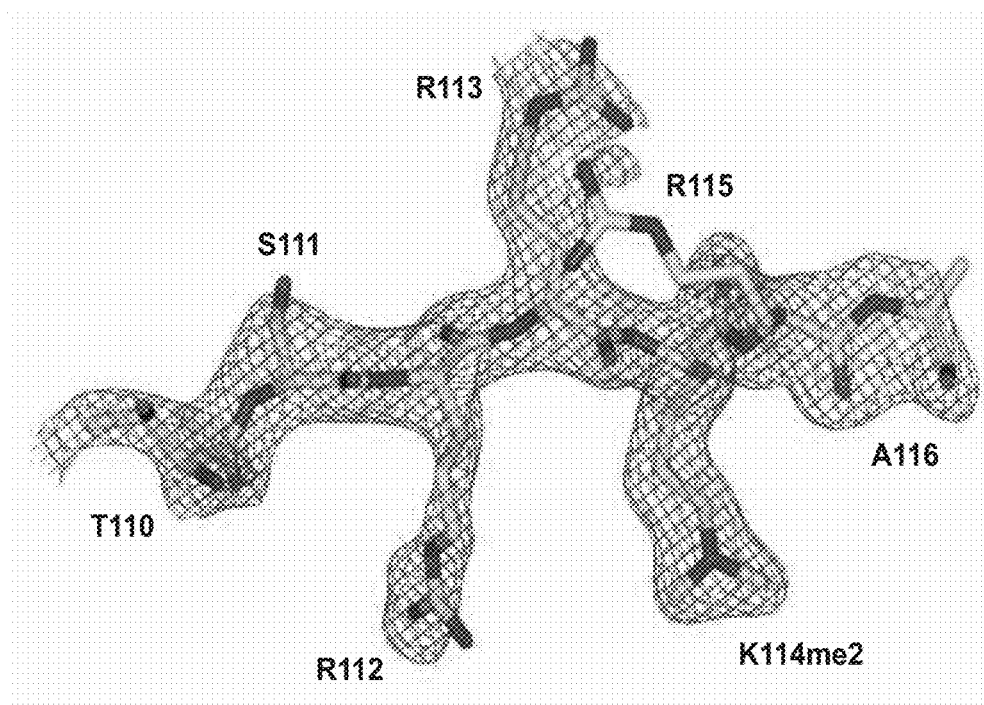
Figure 2:
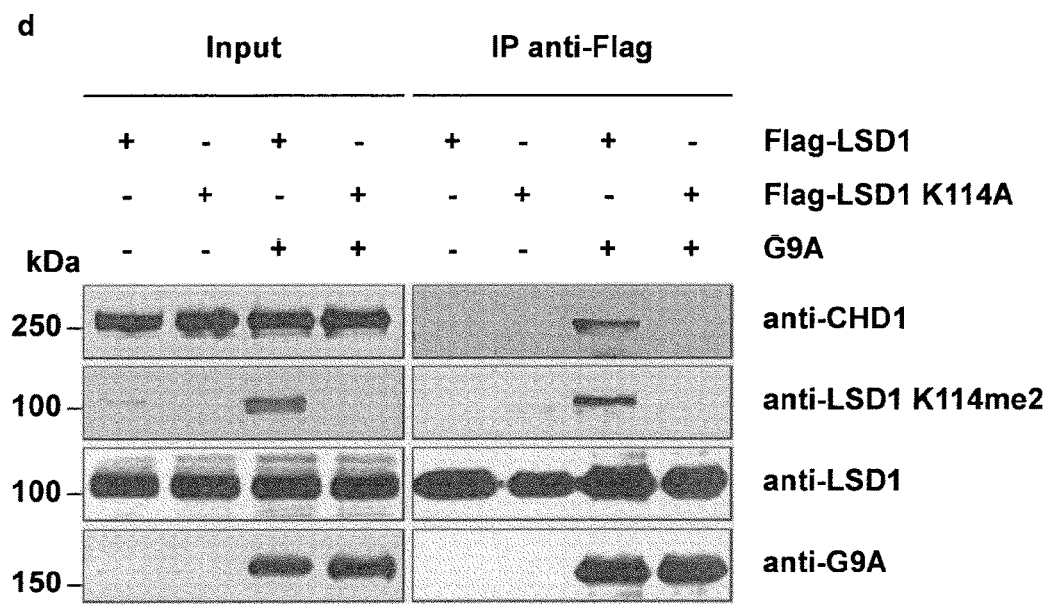
Figure 2:
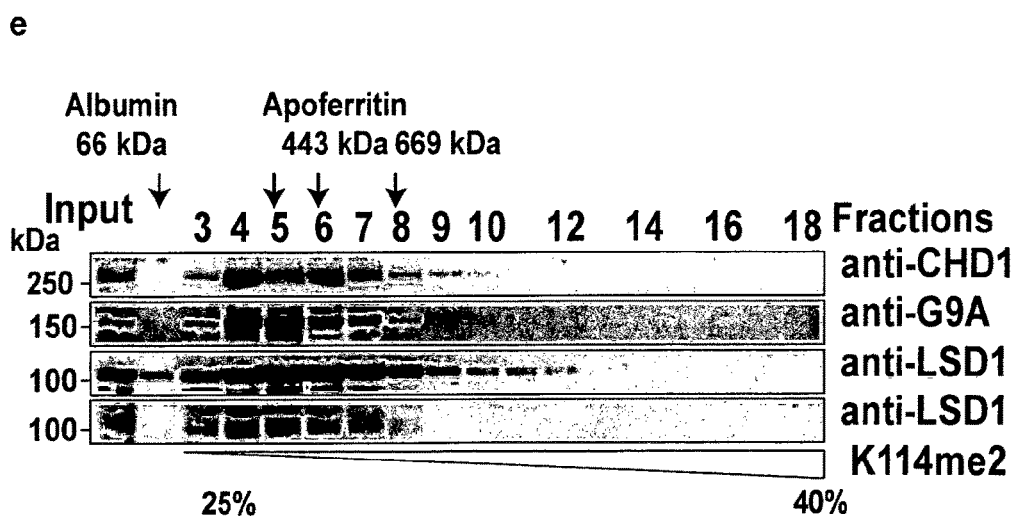
Figure 2:
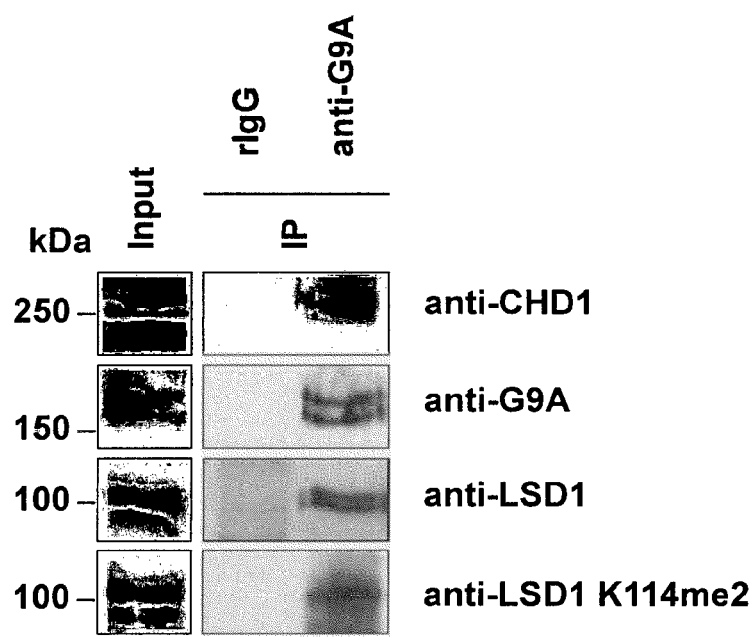

To identify potential LSD1 K114me2 methyl-lysine reader proteins, protein profiling was performed on protein-domain microarrays using un- and dimethylated LSD1 peptides LSD1aa104-127 and LSD1aa104-127 K114me2, respectively (see also ref.[14]). In this profiling assay, several GST-fusion proteins including CHD1 fused to GST were used. Other GST-fusions that were used were e.g. PhD-domain proteins (BPTF, ING2 or PHF2), BROMO-domain proteins (GCN5, TAF1-D1 or TAF1-D2), or BRCT-proteins (BRCA1, 53BP1 or Crb2). Among the proteins present on the microarray, LSD1 K114me2 but not unmethylated LSD1 peptide, specifically interacted with CHD1 double chromodomain (GST-CHD1 Chromo 1/2) indicating that CHD1 is a reader of LSD1 K114me2. Using isothermal titration calorimetry (ITC), the dissociation constants (Kd) of 124 µM, 74 µM, and 82 µM for LSD1 K114me1, me2, and me3 peptides, respectively, were measured (FIG. 2a). These binding affinities are similar to those observed for binding of H3K4me3 peptide to CHD1 (namely a Kd=47 µM, data not shown). Unmethylated LSD1 or H3 peptide did not bind to GST-CHD1 Chromo 1/2 (FIG. 2a).

To investigate the molecular basis for LSD1 K114me2 recognition, the co-crystal structure of CHD1aa270-443 bound to LSD1aa108-119 K114me2 peptide at a resolution of 1.6 Å was solved (FIG. 2b and Supplementary Table 1 shown in the following).

SUPPLEMENTARY TABLE 1

Data collection and Refinement Statistics.

| Data Set | CHD1-LSD1me2 |
|---|---|
| X-ray source | Diamond Light Source, I04 |
| X-ray detector | Dectris Pilatus-6M |
| Wavelength | 0.9795 |
| space group | $P2_12_12$ |
| cell constants a, b, c [Å] | 110.30, 44.44, 46.19 |
| α, β, γ [°] | 90.0, 90.0, 90.0 |
| Molecules in asymmetric unit cell | 1 |
| resolution limits [Å] | 55.15-1.60 |
| | (1.62-1.60) |
| completeness (%) | 98.8 (83.9) |
| unique reflections | 30,650 (1282) |
| multiplicity (%) | 4.4 (4.0) |
| Overall B-factor, Wilson plot (Å$^2$) | 41 |
| $R_{merge}{}^{a)}$ | 0.029 (1.41) |
| $R_{meas}$ | 0.037 (1.79) |
| $R_{p.i.m.}{}^{41}$ | 0.023 (0.84) |
| mean I/σ(I) | 16.4 (0.8) |
| $CC_{1/2}{}^{42}$ | 0.999 (0.554) |
| refinement statistics | |
| $R_{cryst}{}^{b)}$ | 0.228 |
| $R_{free}$ (%) | 0.266 |
| non-hydrogen atoms | 1623 |
| solvent molecules | 89 |
| Cruickshank's DPI$^{43}$ | 0.100 |
| r.m.s. deviations from ideal values | |
| bond lengths (Å) | 0.019 |
| bond angles (°) | 1.91 |

SUPPLEMENTARY TABLE 1-continued

Data collection and Refinement Statistics.

| Data Set | CHD1-LSD1me2 |
|---|---|
| average B values (Å$^2$) | |
| protein main chain atoms | 54.1 |
| protein all atoms | 54.2 |
| solvent | 47.3 |

[a] $R_{merge} = \Sigma_{hkl} [(\Sigma_i |I_i - <I>|)/\Sigma_i I_i]$
[b] $R_{cryst} = \Sigma_{hkl} ||F_{obs}| - |F_{calc}||/\Sigma_{hkl}|F_{obs}|$
$R_{free}$ is the cross-validation R value for a test set of 5% of unique reflections[44].

Amino acid residues 110-116 of the LSD1 peptide were modelled according to the electron density (FIG. 2c). Comparable to the binding of H3K4me3 peptide[15], the LSD1 K114me2 peptide is located at an acidic surface bridging the two chromodomains (FIG. 2b). This interaction involves residues Y295, W322, W325 from chromodomain 1 and D408 and D425 from chromodomain 2 (FIG. 2b and FIG. 5a). The methylammonium group of LSD1 K114 and side chains of W322 and W325 of CHD1 form cation-π interactions. Notably, the side chains of R113 of LSD1 and D425 of CHD1 interact through an ordered water molecule (see FIG. 5a) and superimposition of the crystal structures of CHD1/LSD1 K114me2 and CHD1/H3K4me3 showed that such an interaction cannot occur between CHD1 and H3K4me3 since the residue corresponding to LSD1 R113 is a threonine at position 3 (T3) in H3K4me3 (see FIGS. 5a to c). It was therefore hypothesized that the R113-D425 interaction may be a discriminating feature of CHD1 binding either LSD1 K114me2 or H3K4me3 peptide and that the corresponding surface could be exploited for the design of inhibitors specifically interfering with LSD1 K114me2 but not H3K4me3 interaction (see FIG. 5c). Indeed, mutagenesis of either LSD1 R113 or CHD1 D425 to an alanine (A) abolished the interaction of CHD1 with LSD1 K114me2 peptide, as determined by isothermal titration calorimetry (data not shown). In contrast, the D425A mutation in CHD1 only mildly affected H3K4me3 binding (data not shown). Taken together, these observations suggest the possibility to specifically target the association of CHD1 and LSD1 K114me2 without affecting CHD1/H3K4me3 binding. Next, it was tested whether in vivo the interaction of CHD1 with LSD1 depends on LSD1 methylation. In the presence of G9A, endogenous CHD1 only coimmunoprecipitated with methylated Flag-LSD1, but not with Flag-LSD1 K114A (FIG. 2d). To investigate whether CHD1 and LSD1 K114me2 are present in the same protein complex, LNCaP cell extracts were subjected to sucrose gradient centrifugation. Western blot analyses showed that CHD1, LSD1 K114me2, and G9A co-fractionate, suggesting the existence of a G9A/LSD1 K114me2/CHD1 complex (FIG. 2e). Furthermore, endogenously expressed CHD1 and LSD1 K114me2 coimmunoprecipitated with G9A from LNCaP cell extracts (FIG. 2f). Together, these observations identify CHD1 as a LSD1 K114me2 reader.

4.3. Example 3: CHD1 and AR Chromatin Occupancy is Dependent on LSD1 K114me2

Figure 3:
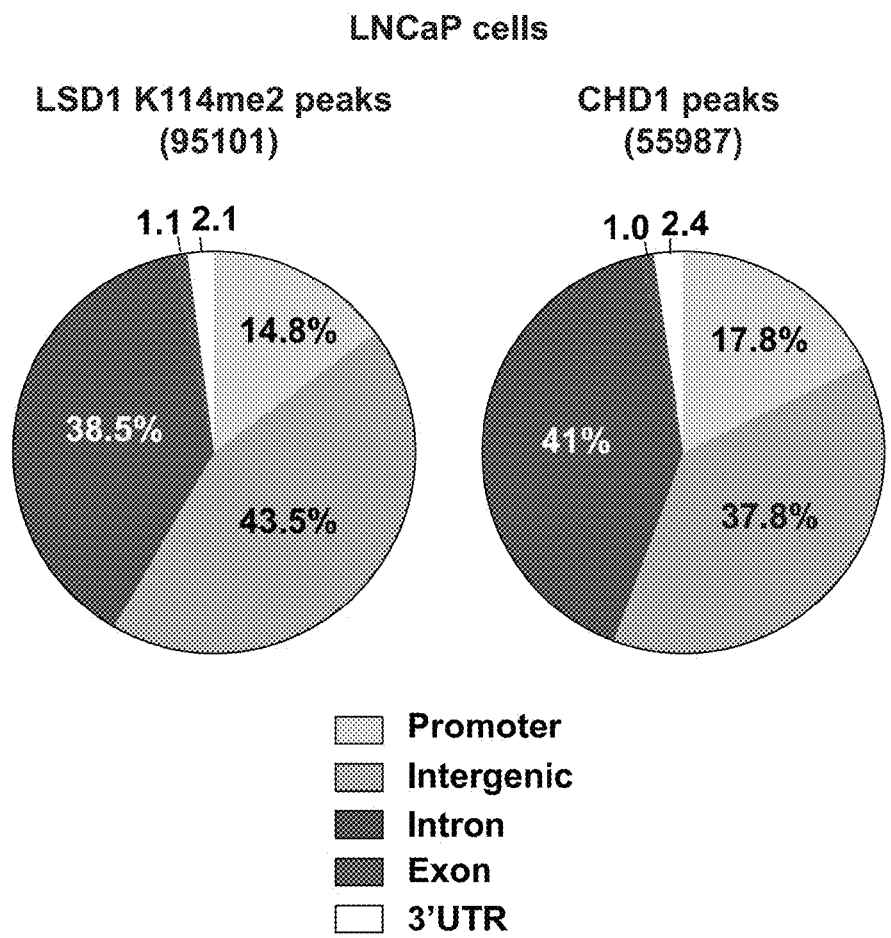
FIG. 3: LSD1 K114me2 controls chromatin binding of AR. (a) Pie charts displaying genomic distribution of LSD1 K114me2 and CHD1 in LNCaP cells cultured in the presence of the AR agonist DHT as determined by ChIP-seq analysis. (b) Venn diagram showing number and intersection of LSD1 K114me2 and CHD1 locations in LNCaP cells cultured in the presence of DHT. (c) Venn diagram showing number and intersection of LSD1 K114me2, CHD1, and AR locations in LNCaP cells cultured in the presence of DHT. (d) Venn diagram showing the intersection and number of genes where LSD1 K114me2 and CHD1 co-localize with genes that are differentially regulated in LNCaP cells upon treatment with DHT. (e,f) Meta-analysis of sequencing read density based on LSD1 K114me2 (e) and CHD1 (f) ChIP-seqs around AR peaks in LNCaP cells cultured in the absence (−DHT) or presence of DHT (+DHT). (g-i) For ChIP, LNCaP cells were cultivated in the presence or absence of DHT, treated with or without Bix-01294 (g) or transfected with siRNA (h, i), as indicated. ChIP analyses were performed with the indicated antibodies. The precipitated chromatin was quantified by qPCR analysis using primers flanking AREs in the enhancer regions of the TMPRSS2 (g,h) or KLK3 (i) genes. (j-l) Treatment with Bix-01294 (j,k) or RNAi-mediated knockdowns of G9A, LSD1, or CHD1 (l) reduces expression of the androgen-regulated TMPRSS2 gene in LNCaP (j,l) and LAPC4 (k) cells. Bars represent mean+SD (n>3). *$p<0.0001$; $p<0.001$; *$p<0.005$ in comparison to cells cultivated in the absence of (−) DHT.
Figure 3:
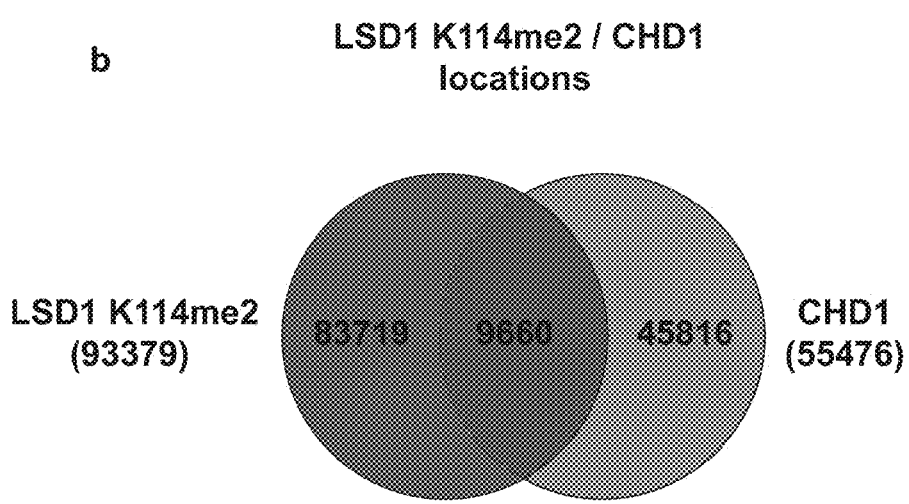
Figure 3:
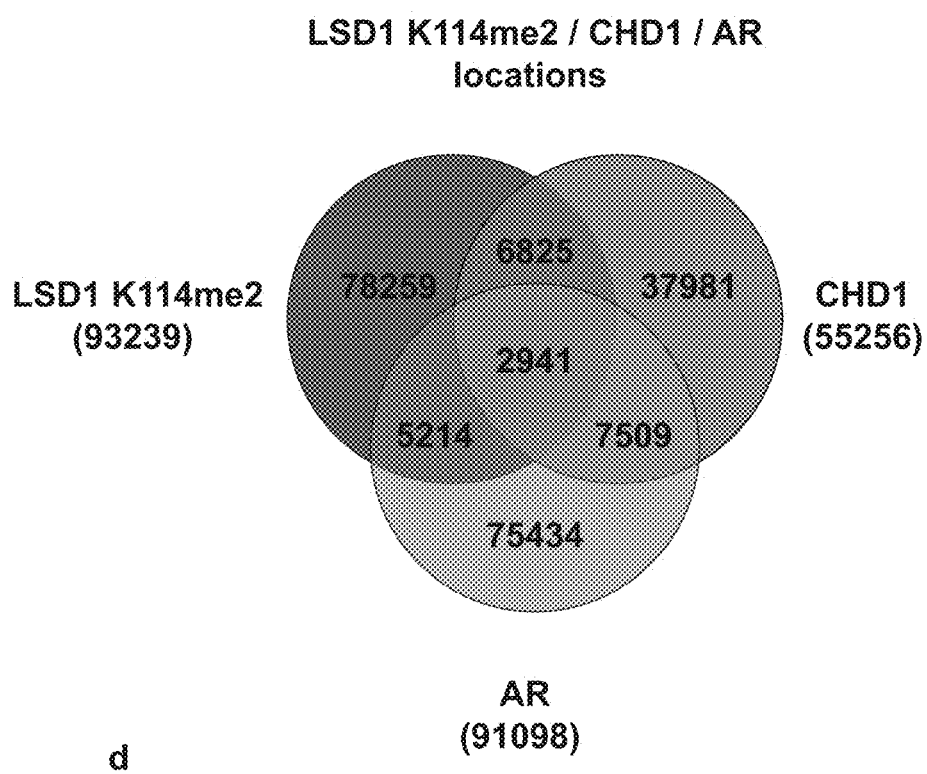
Figure 3:
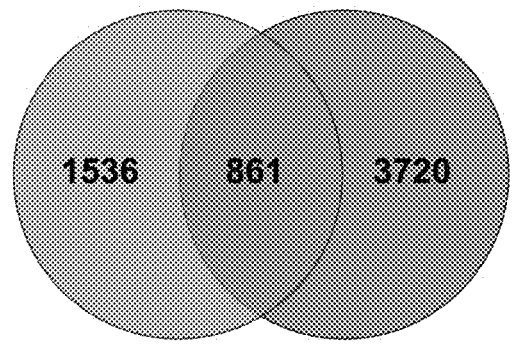
Figure 3:
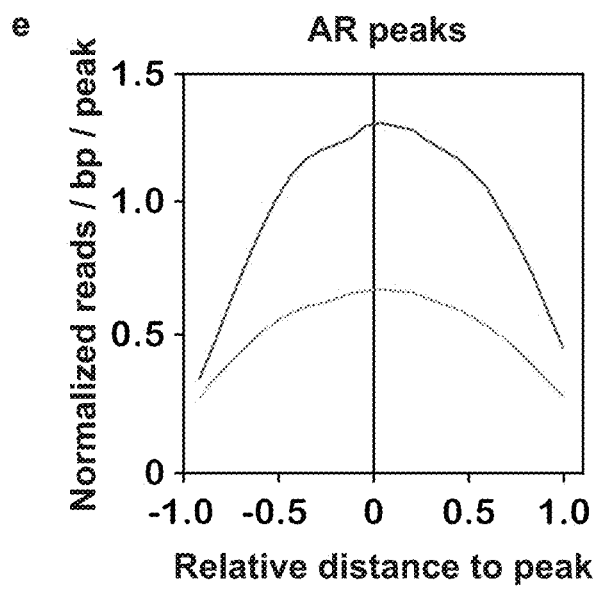
Figure 3:
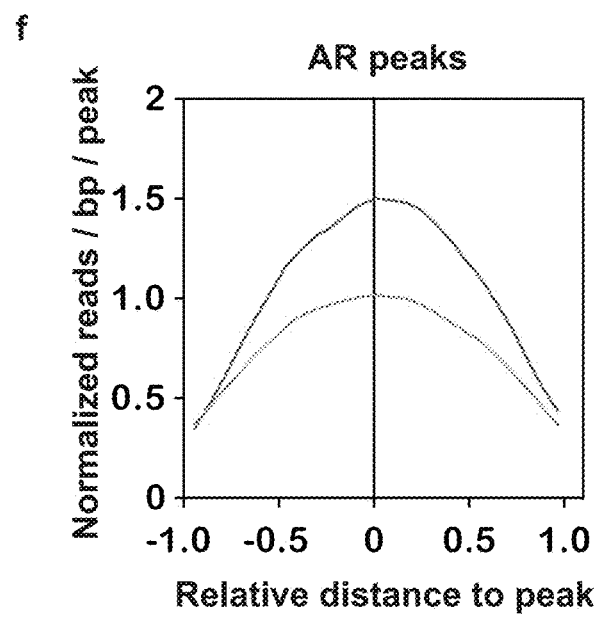
Figure 3:
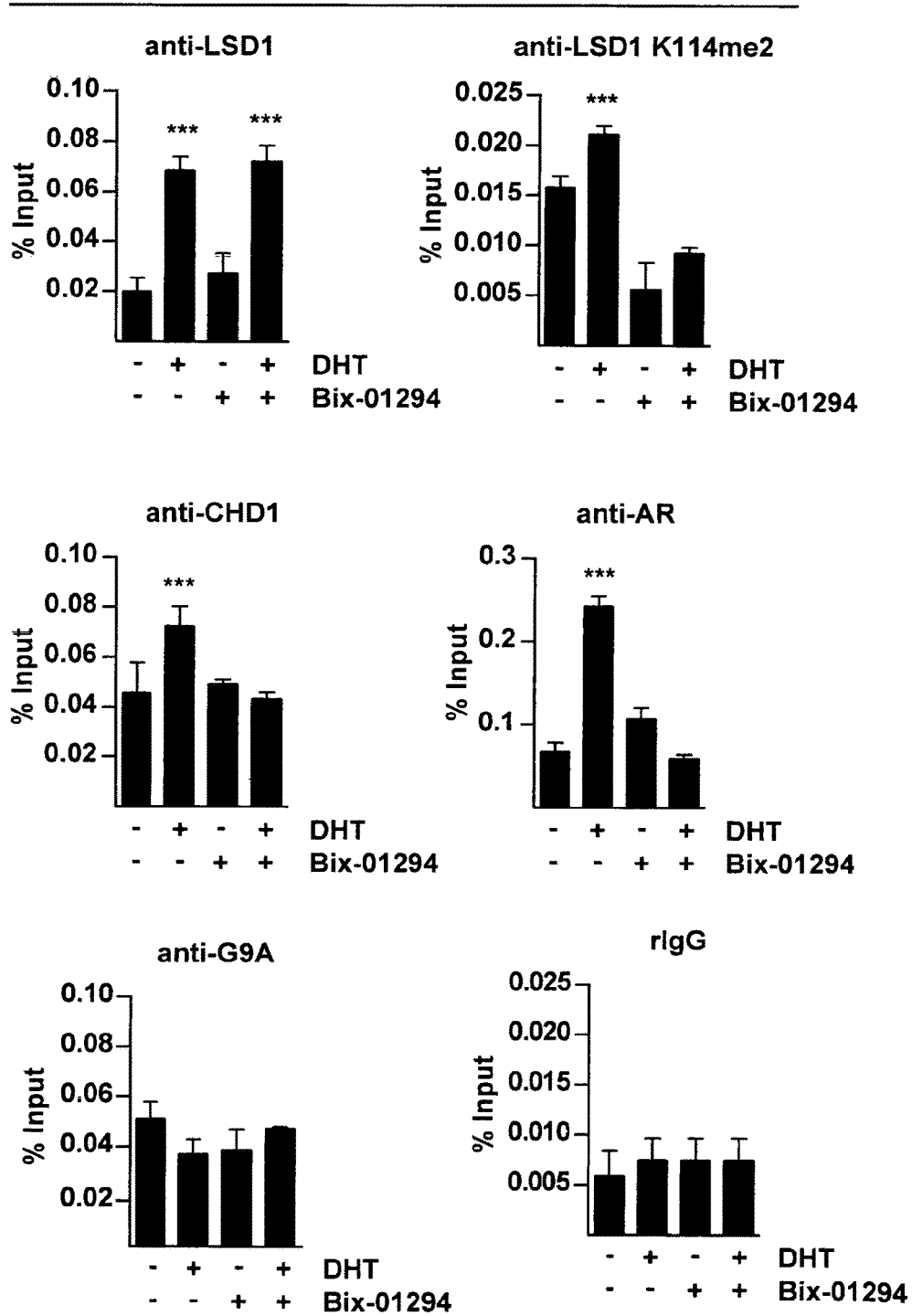
Figure 3:
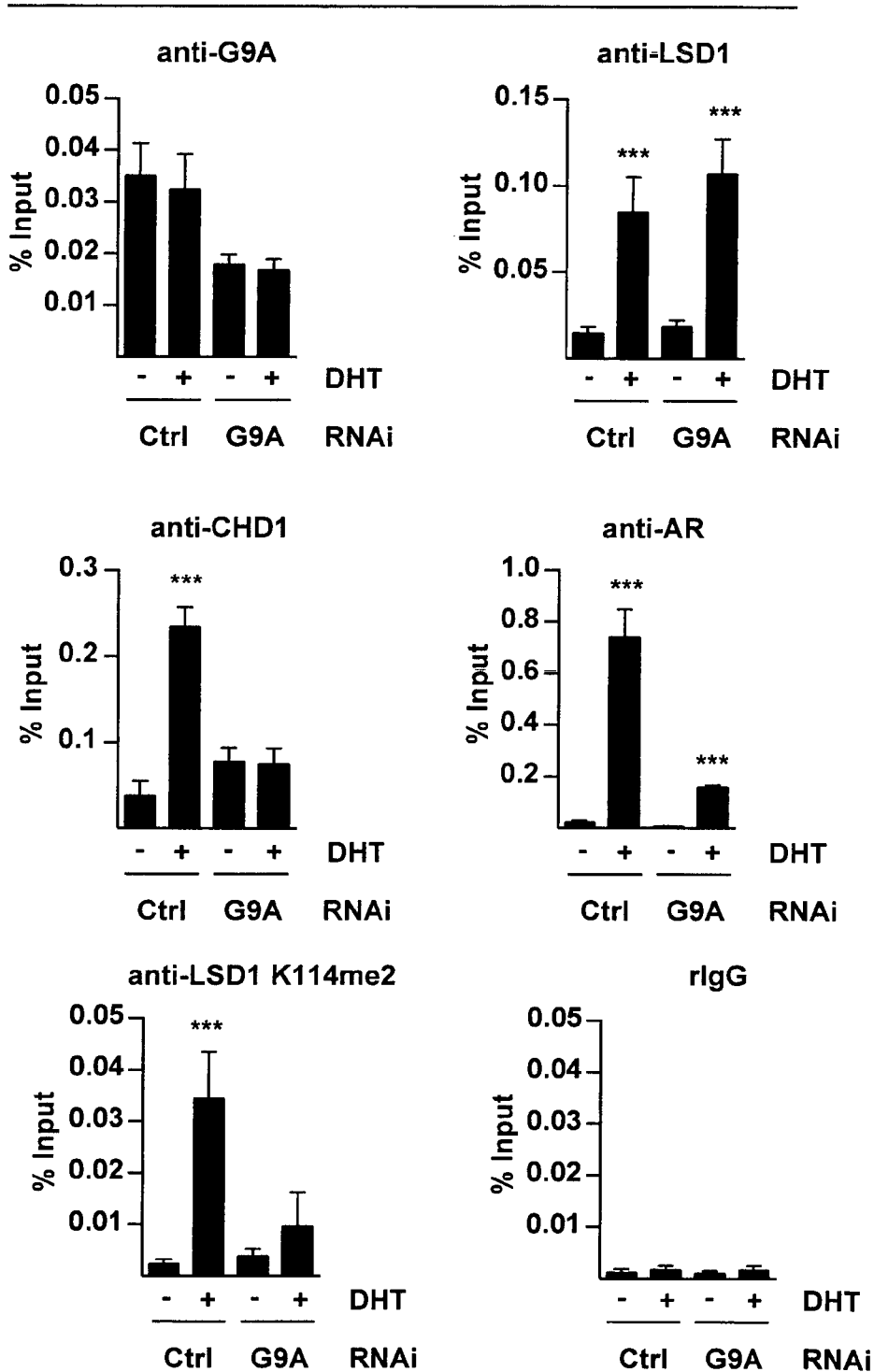
Figure 3:
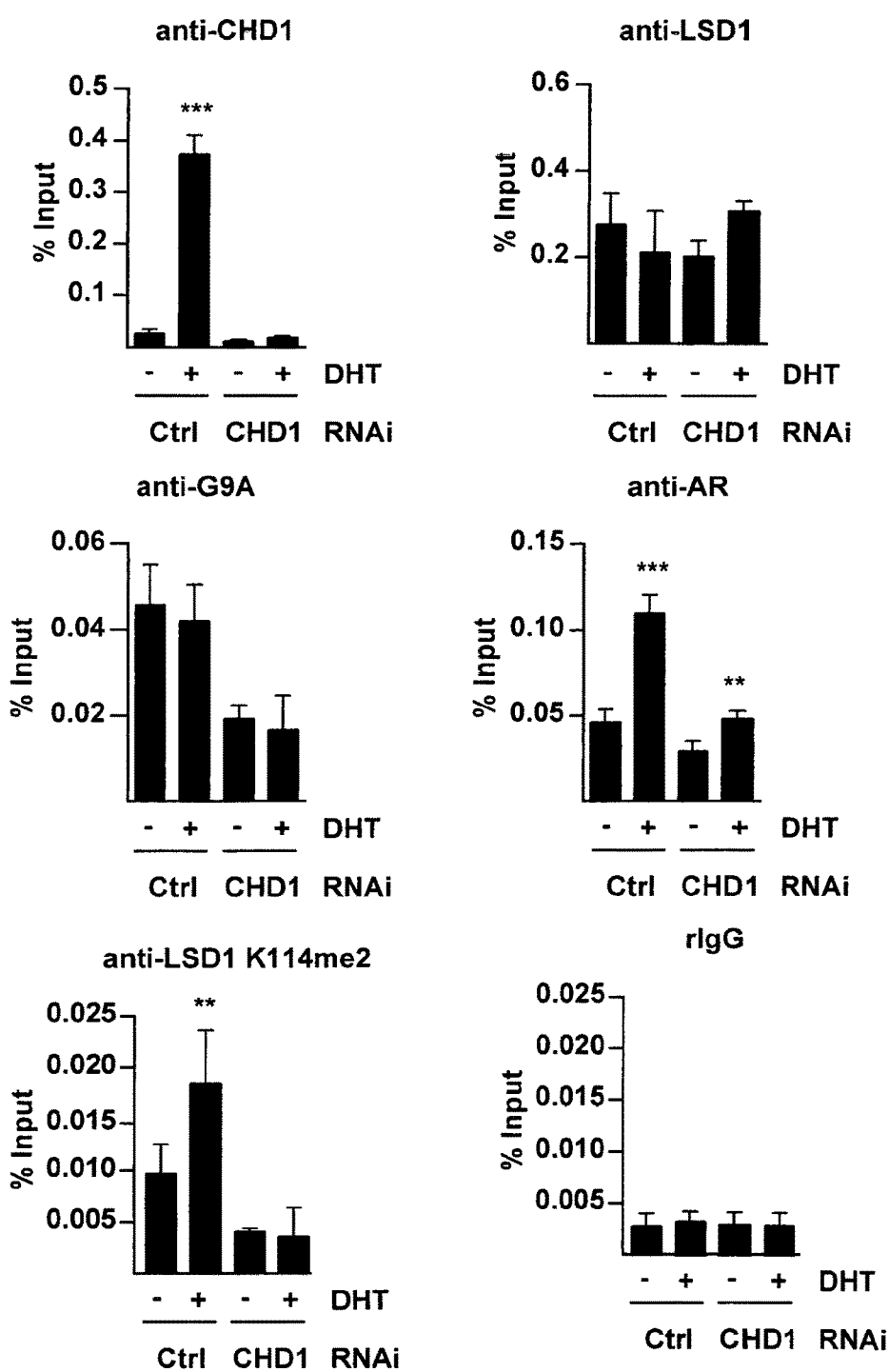
Figure 3:
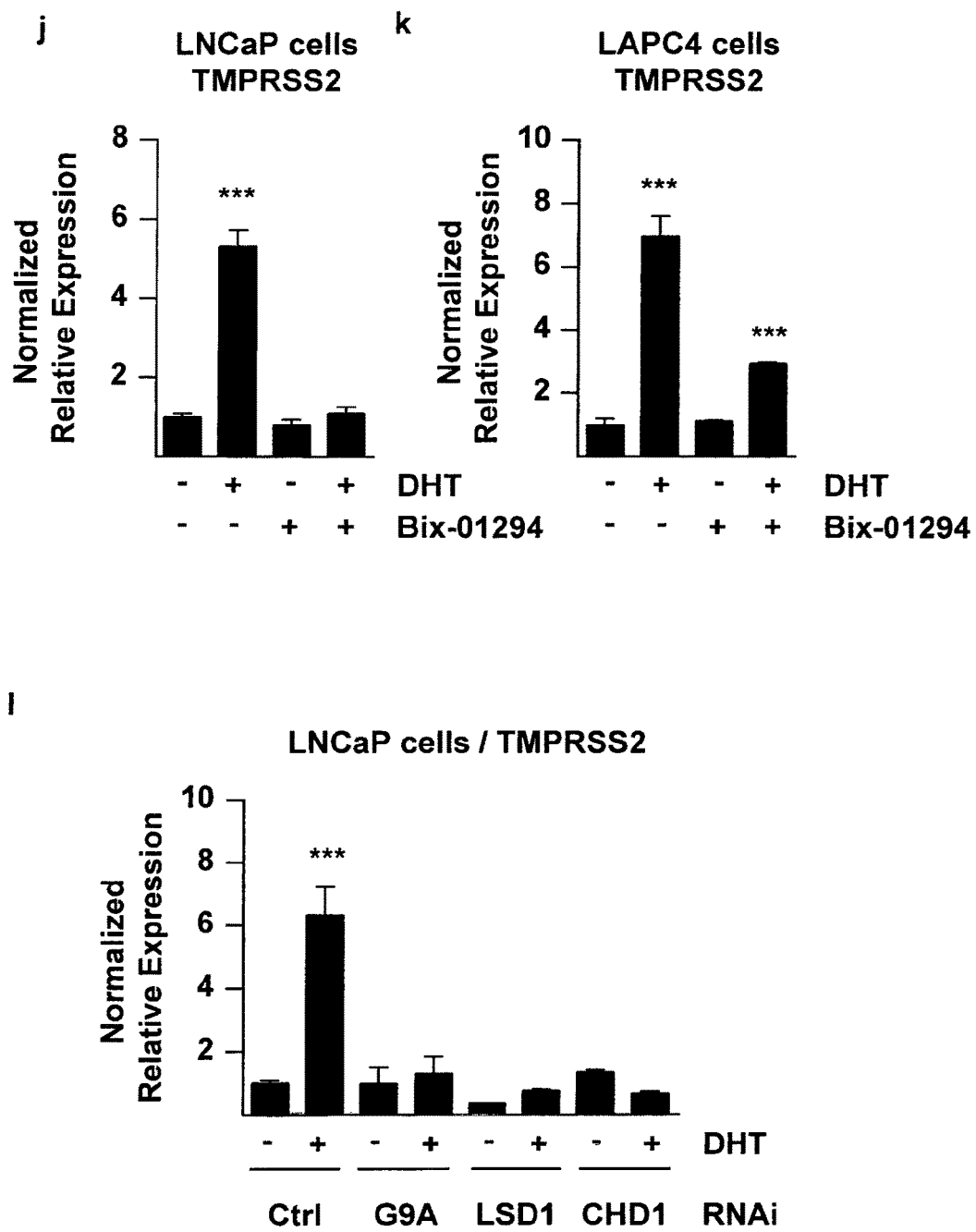

To investigate whether recognition of LSD1 K114me2 by CHD1 on chromatin is involved in androgen-dependent gene regulation, we treated LNCaP cells with the AR agonist dihydrotestosterone (DHT) and performed ChIP-seq with either anti LSD1 K114me2 or anti-CHD1 antibodies. The analyses shown in FIG. 3a identified 95101 high confidence LSD1 K114me2 peaks and 55987 high confidence CHD1 peaks, respectively. The overlap of LSD1 K114me2 with CHD1 locations revealed that 9660 locations are co-occupied (FIG. 3b). Intersection of LSD1 K114me2 and CHD1 cistromes with previously published genome-wide AR binding data[16] revealed that 2941 locations representing 2397 genes are co-occupied (FIG. 3c). To correlate the presence of LSD1 K114me2 and CHD1 peaks with androgen-regulated gene expression, a global transcriptome analysis (RNA-seq) of LNCaP cells cultured in absence or presence of DHT was performed. Among the 2397 genes co-occupied by LSD1 K114me2, CHD1, and AR (FIG. 3c), 861 were differentially regulated upon treatment of LNCaP cells with DHT (FIG. 3d), supporting the idea that LSD1 K114me2/CHD1 interaction plays a role in AR signalling. The bioinformatic analyses indicated an increase of LSD1 K114me2 and CHD1 reads over the AR peaks in DHT compared to vehicle-treated cells (FIG. 3e,f). Based on these observations, it was hypothesized that subsequent to DHT treatment the elevated levels of LSD1 K114me2 and CHD1 at the AR occupied regions might promote binding of AR. To test this idea, LNCaP cells cultured in the presence or absence of DHT and the G9A inhibitor Bix-01294[17] were subjected to ChIP. DHT treatment resulted in elevated LSD1 K114me2 levels accompanied by increased CHD1 and AR occupancy of the TMPRSS2 and KLK3 genes (FIG. 3). Chromatin occupancy of G9A was not altered by the presence or absence of DHT and Bix-01294. Whereas LSD1 enrichment increased upon DHT treatment at the TMPRSS2 enhancer (−13782/−13866), this was not the case at the KLK3 enhancer (−3980/−4048, data not shown). The results are cell type-independent since similar data were obtained with LAPC4 androgen-dependent prostate tumor cells (data not shown). Specificity was controlled for by also using an unrelated region that is not occupied by AR, wherein the effects was not observed. Additionally, chromatin was not enriched when using an IgG control (FIG. 3g). Importantly, when cells were cultured in the presence of Bix-01294, androgen-induced methylation of LSD1 as well as androgen-induced recruitment of CHD1 and AR was blocked (FIG. 3g). Next, it was asked whether knockdown of G9A mimics the observed Bix-01294 effect. Accordingly, LNCaP cells cultured in the presence or absence of DHT were transfected with either an unrelated control siRNA or a siRNA directed against G9A and subjected to ChIP. Similar to the treatment with Bix-01294, ligand-induced methylation of LSD1 at K114, as well as recruitment of CHD1 and AR, was robustly impaired upon knockdown of G9A (FIG. 3h). Together, these data indicate that CHD1 and AR chromatin occupancy is critically dependent on LSD1 K114me2.

4.4. Example 4: The Presence of LSD1 K114me2 and CHD1 Promotes Chromating Binding of AR During AR-Dependent Gene Expression To further decipher the mechanism underlying DHT-induced methylation of LSD1, binding of CHD1 to LSD1 K114me2, and recruitment of AR to androgen response elements (AREs) we performed CHD1 RNAi. Loss of CHD1 did not affect chromatin occupancy of LSD1 but severely reduced methylation of LSD1, which correlates with loss of G9A and block of ligand-induced AR recruitment (FIG. 3i). These data clearly demonstrate that AR binding to AREs not only requires methylation of LSD1, but also the presence of CHD1. Next, the effect of Bix-01294 treatment on the expression of representatives of the 2397 AR target genes that show co-localization of AR, LSD1

K114me2, and CHD1 was analyzed. DHT-induced expression of genes such as TMPRSS2, KLK3, PRDM4, ELK4, GREB1, IGF1R, FKBP5, or EGFR was greatly reduced upon treatment of LNCaP or LAPC4 cells with Bix-01294 (FIG. 3j,k). Similarly, robust effects were observed upon RNAi mediated knockdown of G9A, LSD1, or CHD1 (FIG. 3l). In summary, the results reveal that during AR-dependent gene expression, methylation of LSD1 at K114 by G9A and recruitment of CHD1 to AR binding regions is a key event controlling chromatin binding of AR.

Figure 4:
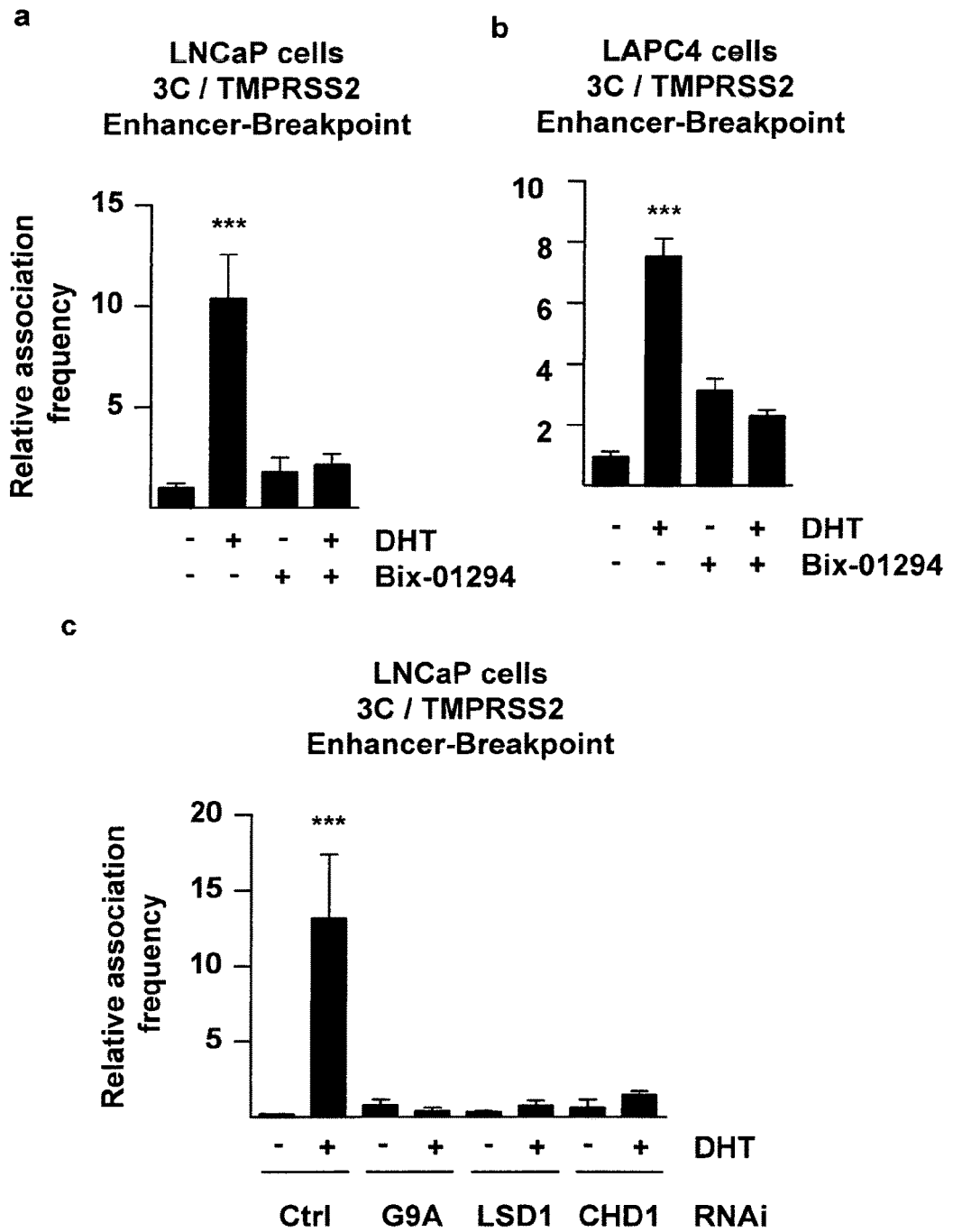
FIG. 4: LSD1 K114me2 controls TMPRSS2-ERG fusion. (a-e) For 3C experiments, LNCaP (a,c) and LAPC4 (b) cells were cultivated in the presence or absence of DHT, treated with or without Bix-01294 (a,b) or transfected with siRNA (c), as indicated. (d,e) LNCaP cells expressing RNAi resistant (rr) Flag NLS LSD1-IT, Flag NLS LSD1-rr K114A (d), CHD1-rr, or CHD1-rr D425A (e), treated with siRNA as indicated in the presence or absence of DHT were subjected to 3C. (f) TMPRSS2-ERG expression was analyzed in LNCaP cells cultivated in the presence or absence of DHT and transfected with siRNA as indicated. (g) TMPRSS2-ERG fusion was analyzed by FISH in LNCaP cells cultivated in the presence or absence of DHT and transfected with siRNA as indicated. ERG break-apart is indicated (white arrow). Bars represent mean+SD (n>3). *$p<0.0001$; $p<0.001$; *$p<0.005$ in comparison to cells cultured in the absence of (−) DHT (a-f).
Figure 4:
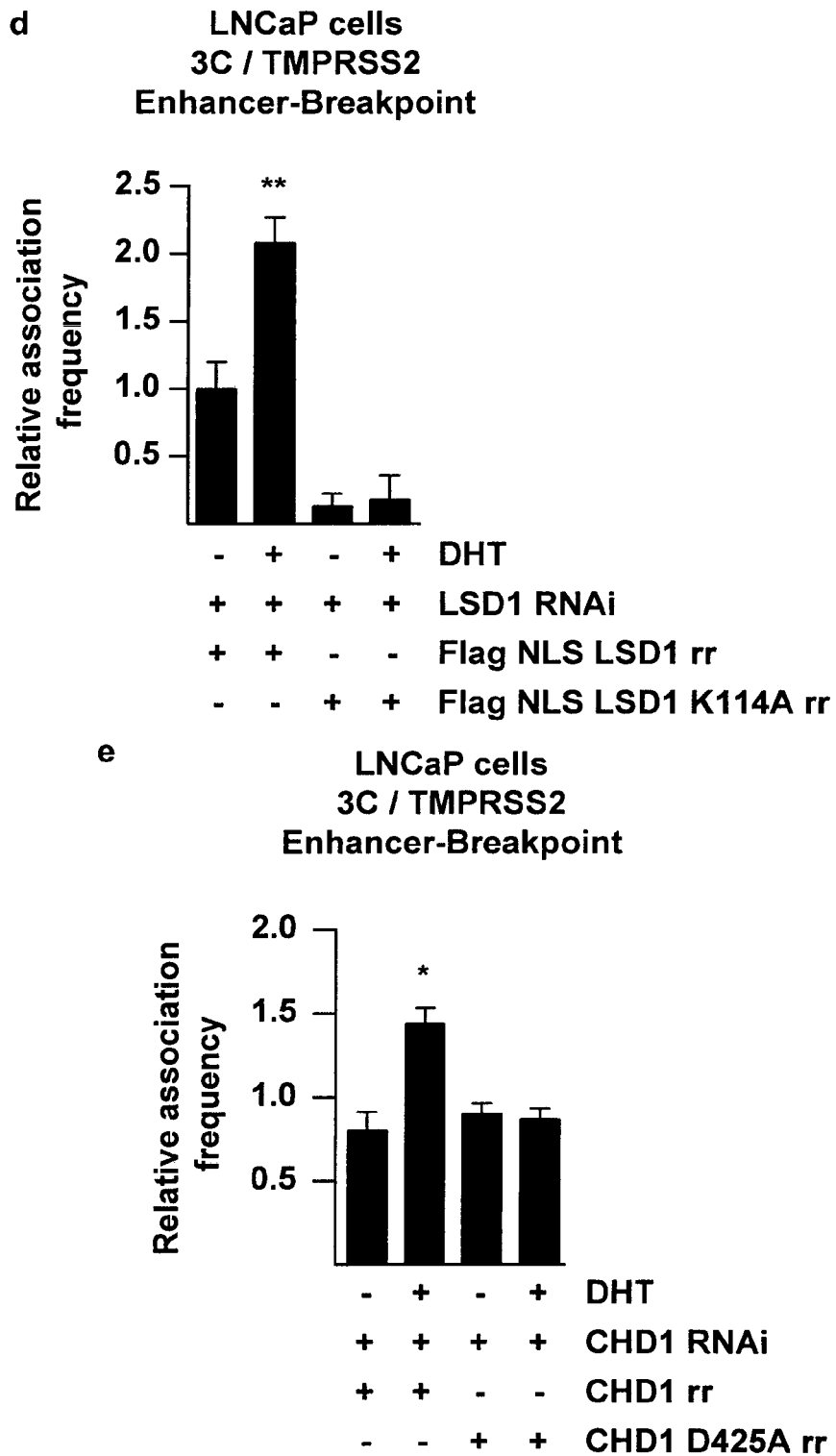
Figure 4:
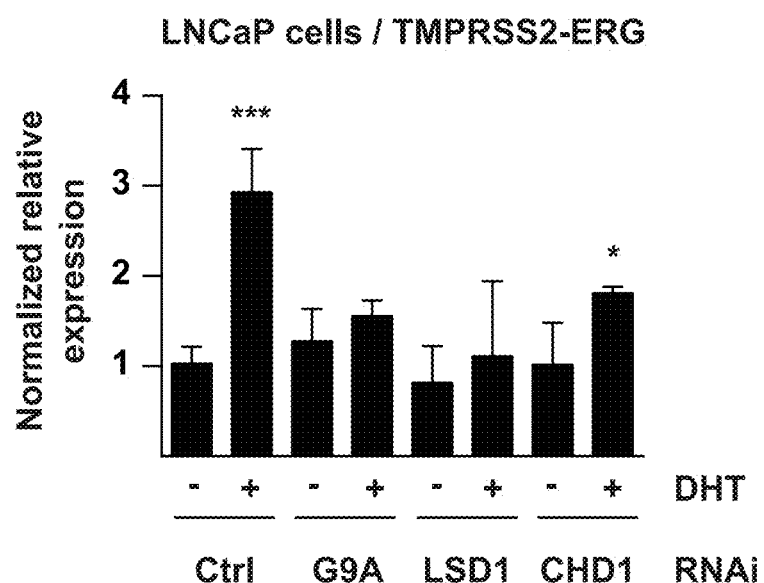
Figure 4:
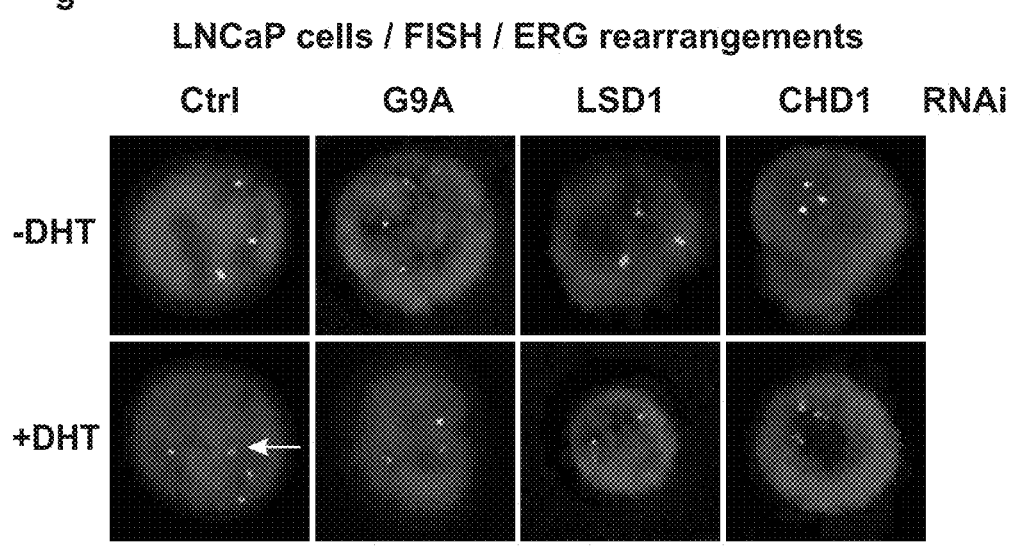

4.5. Example 5: DHT-Induced Chromosomal Conformational Changes at the TMPRSS2 Enhancer-Breakpoint Regions Need the Integrity of the G9A/LSD1 K114me2/CHD1 Circuit Since it was shown that androgen-dependent methylation of LSD1 at K114 by G9A and recruitment of CHD1 control binding of AR at the enhancer of the TMPRSS2 gene, it was tested whether AR transcription-associated genomic translocations such as TMPRSS2-ERG fusion are controlled by LSD1 K114 methylation. It has been shown that androgen-induced binding of AR to AREs causes chromosomal conformational changes resulting in looped chromatin necessary for coordinated transcription[18]. At the TMPRSS2 locus, such chromosomal interactions involve the looping of the enhancer region with a region in intron 1 where genomic breaks occur during the generation of TMPRSS2-ERG gene fusion[4]. To elucidate whether LSD1 K114me2 might control androgen-dependent TMPRSS2 enhancer-breakpoint loop formation LNCaP cells were cultured in the absence and presence of DHT and subjected to chromosome conformation capture (3C) analysis. In agreement with a previous report[4], enhancer-breakpoint interactions upon treatment with DHT was observed. Importantly, however, treatment with Bix-01294 blocked this loop formation in LNCaP and LAPC4 cells demonstrating that methylation of LSD1 is necessary for TMPRSS2 enhancer-breakpoint loop formation (FIG. 4a,b). In corroboration, knockdown of either G9A, LSD1, or CHD1 also robustly impaired androgen-induced looping (FIG. 4c). To further highlight the importance of LSD1 K114me2 in the control of TMPRSS2 enhancer-breakpoint loop formation, it was tested whether androgen-dependent loop formation is compromised in presence of the LSD1 K114A mutant. Therefore, LNCaP cells expressing RNAi resistant (rr) Flag-NLS-LSD1-rr and Flag-NLS-LSD1-rr K114A constructs were generated. Upon knockdown of endogenous LSD1, DHT-induced looping was observed in LNCaP cells expressing Flag-NLS-LSD1-rr but not in the cells expressing the Flag-NLS LSD1-rr K114A mutant (FIG. 4d). These data further highlight the importance of LSD1 methylation at K114 for the formation of androgen-dependent chromatin loops. In a similar approach, it was tested whether the mutant protein CHD1 D425A, which fails to interact with LSD1 K114me2 peptide, impairs androgen-dependent chromatin looping. Consequently, LNCaP cells expressing RNAi resistant CHD1-rr and CHD1-rr D425A were generated. Knockdown of endogenous CHD1 allows DHT-induced looping in LNCaP cells expressing CHD1-rr but not in the cells expressing the CHD1-rr D425 mutant protein demonstrating the importance of D425 of CHD1 for the interaction with methylated LSD1 and subsequent loop formation (FIG. 4e). Together, these data demonstrate that DHT-induced chromosomal conformational changes observed at the TMPRSS2 enhancer-breakpoint regions need the integrity of the G9A/LSD1 K114me2/CHD1 circuit. Recently, Haffner et al. reported that DHT-treatment alone is sufficient to induce TMPRSS2-ERG fusion in a small proportion of prostate cells[4]. Thus, it was wondered whether DHT-induced TMPRSS2-ERG fusion depends on LSD1 K114me2 and, if so, might be blocked upon knockdown of LSD1, G9A, or CHD1. Consistant with Haffner et al., DHT-treatment of LNCaP cells led to the production of TMPRSS2-ERG transcript and induced ERG rearrangements, as observed by FISH (FIG. 4f,g). Knockdown of either G9A, LSD1, or CHD1 severely reduced DHTinduced expression of TMPRSS2-ERG transcripts and, importantly, TMPRRS2-ERG gene rearrangements were blocked (FIG. 4f,g).

4.6. Example 6: Methods and References

Plasmids:

Flag-LSD1 and GST-LSD1 were described previously[19]. Flag-G9A was provided by Y. Shinkai. Flag-LSD1 K114A was obtained by site directed mutagenesis. To construct expressions plasmids for GST-LSD1, GST-LSD1 K114A, or CHD1aa270-443, the corresponding cDNA fragments were cloned into pFast-Bac-HT-GST A, pDEST20, or pET15b.

Chromatin Immunoprecipitation (ChIP):

ChIP experiments were performed essentially as previously described[10]. LNCaP and LAPC4 cells were cultured for 210 min in the absence or presence of 1×10-7 M DHT as indicated. Three days before harvesting, cells were transfected with siRNA against LSD110, G9A20, or CHD121 that were previously described and validated using Dharmafect2 (Thermo Scientific) following the manufacturer's instructions. Immunoprecipitation was performed with specific antibodies (α-AR (N-20), #sc-816, lot A0207, Santa Cruz), α-LSD1 (#20752, Schuele Laboratory), α-LSD1 K114me2 (#4871, Schuele Laboratory), α-CHD1 (#A301-218A, lot A301-218A-1, Bethyl Laboratories), α-G9A (#ab40542, lot GR170862-1, Abcam) on protein A-Sepharose 4B (GE-Healthcare). For PCR, 2 µl out of 70 µl DNA extract were used. Primer sequences were as follows: TMPRSS2 enhancer (−13782/−13866) 5'-GCCACCTGGT-GAAGTGCAGA-3' (SEQ ID NO:1) and 5'-TG-GAGCTAGTGCTGCATGTC-3' (SEQ ID NO:2); KLK3 enhancer (−3980/−4048) 5'-TTATCTAGGACAG-TAAGCAAGCC-3' (SEQ ID NO:3) and 5'-GGATGTTTG-TAAAGCAGGCAT-3' (SEQ ID NO:4); control (chr6: 151953789-151953927) 5'-TCCTAATGACATTTGATGTTCAGC-3' (SEQ ID NO:5) and 5'-CCCTTAAAAGTCAACAACAAGA-3' (SEQ ID NO:6).

ChIP Sequencing (ChIP-Seq):

Libraries were prepared from immunoprecipitated DNA according to standard methods. ChIP-seq libraries were sequenced using a HiSeq 2000 (Illumina) and mapped to the hg19 reference genome using bowtie 2[22]. Data were further analyzed using the peak finding algorithm MACS 1.41[23] using input as control. All peaks with FDR greater than 1% were excluded from further analysis. The uniquely mapped reads were used to generate the genome-wide intensity profiles, which were visualized using the IGV genome browser[24]. HOMER[25] was used to annotate peaks, to calculate overlaps between different peak files, and for motif searches. The genomic features (promoter, exon, intron, 3'UTR, and intergenic regions) were defined and calculated using Refseq and HOMER. Previously reported ChIP-seq results for AR (GSE28264) were used for analysis.

Western Blot Analysis:

Experiments were performed as previously described[10].

Methylation Assay:

One µg of purified recombinant GST-LSD1 or GST-LSD1 K114A were incubated with 1 µg of purified recombinant GST-G9Aaa786-1210) (Reaction Biology Corp.) in the presence of 160 µM S-adenosyl-methionine (New England BioLabs) as indicated in methylation buffer (50 mM Tris HCl pH 8.5, 50 mM NaCl, 5 mM MgCl2, 1 mM DTT, and protease inhibitor cocktail (Roche)) for 120 min at 37° C. The reaction mixture was analyzed by Western blotting using antibodies as indicated.

Isothermal Titration Calorimetry (ITC):

ITC experiments were performed at 25° C. with a Micro-Cal VP-ITC microcalorimeter (GE Healthcare). Experiments were performed by injecting 12 µl of peptide (1.5 mM) into the sample cell containing 100 µM CHD1 in 20 mM BTP pH 8, 75 mM NaCl. A total of 24 injections were performed with a spacing of 240 s and a reference power of µcal s$^{-1}$. Automated baseline assignment and peak integration were performed with NITPIC version 1.0.1.[26]. Isotherms were plotted, with a single-site binding model, using SEDPHAT version 10.58d[26]. Isotherms were subsequently validated by one dimensional error surface projections in SEDFIT[27].

X-Ray Crystallography:

The CHD1-LSD1 complex was formed by mixing CHD1 (14 mg ml$^{-1}$) with an eightfold molar excess of LSD1aa108-119 K114me2 peptide. Crystals (space group P21212) were grown by sitting drop vapour diffusion at 4° C. in buffer containing 100 mM Hepes pH 7.5, 0.2 M L-proline, 10% (w/v) PEG3350. Prior to flash cooling in liquid nitrogen, crystals were cryoprotected in reservoir solution with 20% (v/v) ethylene glycol. Initial X-ray diffraction data were collected at the PXI beamline at the Swiss Light Source at 1=1.000 Å with a Pilatus detector. The data set for the final refined model was collected at a 100K at beamline I04 at Diamond Light Source. Data were processed and analyzed with XDS28 and Aimless[29]. The structure was solved by molecular replacement with Phaser[30] using 2B2W as a search model. Manual building and refinement were performed using Coot31 and Refmac532 in the CCP4 program suite[33]. Supplementary Table 1 summarises the statistics for data collection and refinement. Structural figures were generated in PyMOL.

RNA Preparation and Analysis:

RNA was isolated with TRIzol Reagent (Invitrogen). Two micrograms of RNA were converted to cDNA with SuperScript II reverse transcriptase (Invitrogen) and polyT oligonucleotides according to the supplier's protocol. Quantitative RT-PCR was performed using the Abgene SYBR Green PCR kit (Invitrogen) according to the supplier's protocol. HPRT was used for normalization. Primer sequences for HPRT, TMPRSS2, KLK3, PRDM4, ELK4, GREB1, IGF1R, FKBP5, and EGFR were described previously[19].

TMPRSS2-ERG Expression Analysis:

Expression analysis of TMPRSS2-ERG (FIG. 4f) was done essentially as previously described. RNA was isolated from LNCAP cells and first strand synthesis was carried out using Superscript II (Life Technologies) with primers specific to ERG (5'-AACTGCCAAAGCTGGATCTG-3') (SEQ ID NO:7) and HPRT (5'-CCAGGTAGCTGGGTTACAGG-3') (SEQ ID NO:8) according to the supplier's protocol. Probes were analyzed on a Roche LightCycler®480 by TaqMan-based qPCR using primers and probes specific for TMPRSS-ERG (#4331182, Life Technologies) and HPRT (#4331182, Life Technologies). HPRT was used for normalization.

RNA Sequencing (RNA-Seq):

RNA samples were sequenced by the standard Illumina protocol to create raw sequence files (.fastq files) at the sequencing core facility of the DKFZ. These reads were aligned to the hg19 build of the human genome using TopHat version 2[34]. The aligned reads were counted with the homer software (analyze RNA) and DEG's were identified using EdgeR[35] and DESeq version 1.8.3[36].

Stable Isotope Labelling by Amino Acids in Cell Culture (SILAC):

For SILAC, LNCaP cells were cultured for six passages in SILAC Dulbecco's modified Eagle's medium (Silantes) containing 10% dialyzed fetal bovine serum (Silantes), penicillin/streptomycin (Life Technologies) and glutamine (Life Technologies) and were labeled with either L-lysine and L-arginine (Lys0, Arg0, Silantes) or L-lysine$^{13}$C$_6$-$^{15}$N$_2$ and L-arginine$^{13}$C$_6$-$^{15}$N$_4$ (Lys8, Arg10, Silantes).

PCP-SILAC and Mass Spectrometry:

Protein correlation profiling (PCP) was essentially done as described[37]. Light (Lys0, Arg0) and heavy (Lys8, Lys10) labelled LNCaP cells were harvested and resuspended in nuclear isolation buffer (10 mM HEPES-KOH pH 7.9, 1.5 mM MgCl2, 10 mM KCl, 0.5 mM DTT, Complete protease inhibitor cocktail, Roche), allowed to swell on ice for 10 min, vortexted for 10 seconds at low speed, and pelleted. Isolated nuclei were resuspended in nuclear disruption buffer (20 mM HEPES-KOH pH 7.9, 25% glycerol, 420 mM NaCl, 1.5 mM MgCl2, 0.2 mM EDTA, 0.5 mM DTT, Complete protease inhibitor cocktail), remained on ice for 20 min and centrifuged at 14 000 rpm for 10 min. The supernatants comprising the nuclear extracts of heavy and light cells were collected, and applied to a sucrose gradient made up of 5 times 1.5 ml fractions of sucrose ranging from 25 to 40% (50 mM Tris-HCl pH 8.0, 100 mM NaCl, Complete protease inhibitor cocktail, sucrose in varying concentrations). Protein complexes were separated on the gradient at 36 000 rpm for 14 h and fractions of 1 ml were collected.

The Lys0/Arg0 PCP-SILAC fractions were combined and spiked in a 1:1 ratio to the respective Lys8/Arg10 PCP-SILAC fractions. The resulting fractions were resuspended in SDS loading buffer, reduced and alkylated with DTT (Sigma-Aldrich) and iodoacetamide (Sigma-Aldrich), respectively. The fractions were then concentrated with a 10 kDa cut-off filter. Protein mixtures were separated by SDSPAGE (4-12% Bis-Tris gradient gel, NuPAGE; Life Technologies) and in-gel digested with trypsin (Promega) at 37° C. ON. All peptide fractions were analyzed using an LTQ Orbitrap XL mass spectrometer (Thermo Fisher Scientific) coupled to an Agilent 1200 (Agilent Technologies) or an Eksigent 2D nanoflow-HPLC (AB Sciex). The reverse phase HPLC column was self-packed in a fused silica capillary (ReproSil-Pur® 3 µm) with 75 µm inner diameter to a length of 25 cm. Peptides were loaded onto the LC-system by an autosampler and separated by a gradient of buffer A (0.5% acetic acid in water) and buffer B (0.5% acetic acid in 80% ACN/water) with increasing organic proportion (loading of sample with 2% of solvent B; first separation ramp from 2 to 30% B within 105 min, and second ramp from 30 to 80% B within 10 min).

The mass spectrometer was operated in the data-dependent mode. Following the survey scan of 1×106 ions in the Orbitrap, the five most abundant multiply-charged ions were fragmented in the linear ion trap using 35% collision energy and a target value of 5000. Parent ions with a charge state of z=1 and unassigned charge states were excluded for fragmentation. Further MS/MS settings were: repeat duration (30 s), repeat count (1), exclusion duration (90 s), and isolation width (2). For MS/MS wideband activation was enabled. Remaining settings were set to default. The mass range for MS was m/z=350 to 2000, and signal threshold was 1000. The resolution was set to 60000. Mass-spectrometric parameters were as follows: spray voltage 2.3 kV; no sheath and auxiliary gas flow; ion-transfer tube temperature 200° C.

Mass Spectrometric Data Analysis:

Raw files were analyzed with the MaxQuant software (version 1.4.1.2.)[38,39]. Cysteine carbamidomethylation was set as fixed modification, methionine oxidation, protein amino-terminal acetylation and pyro-glutamate and pyro-glutamic acid formation from glutamate and glutamic acid, respectively, were set as variable modifications. Double SILAC was chosen as quantification mode. Two miss cleavages were allowed, enzyme specificity was trypsin/P, precursor ion mass tolerance was 20 ppm for first search, and fragment ion mass tolerance was 0.5 Da for MS/MS spectra. A false discovery rate (FDR) of smaller 1% on peptide and protein level was determined by using a forward-reverse decoy database (Uniprot Human, version July 2014). A minimum length of seven amino acids per peptide was used. Both unmodified and modified and both razor and unique peptides with a minimum ratio count of 2 were used for protein quantification.

Cluster Analysis:

The proteins were only included in cluster analysis if respective peptides were sequenced in each of the eight fractions yielding eight data point profiles. As an additional quality criterion profiles were checked for apparent outliers. Protein profiles were defined as outliers when their summed ratios were not within the range of three times the standard deviation of the average summed ratio, and removed from datasets before cluster analysis. The protein ratios were normalized using the base 2 logarithm. Clustering was done with the k-means algorithm. To define the appropriate number of centroids for cluster analysis the algorithm was run multiple times with initial randomly selected cluster centers and checked for consistent results. Optimal configuration was obtained with a k value of 20 centroids and applied in the present analysis.

Cell Culture:

LNCaP cells were cultured and transfected as described[10]. 293T cells were cultured in DMEM and LAPC4 in IMDM supplemented with 10% FCS glutamine and penicillin/streptomycin. Ten μg of expression plasmid coding for Flag-LSD1, Flag-LSD1 K114A, or Flag-G9A were transfected per 293T dish and cultivated for 24 hours before harvesting (FIG. 1b). Three days before harvesting for ChIP (FIG. 3g-i), ChIP-seq (FIG. 3a), Western blot analysis, expression analysis (FIG. 3k), or 3C (FIG. 4c,d,e), LNCaP cells were transfected with siRNA. For FISH and analysis of TMPRSS2-ERG expression (FIG. 4f,g) cells were transfected with siRNAs height and five days before harvesting; DHT $10^{-6}$ M was added to the cells as indicated 3 days before harvesting. Cells were cultivated for 72 hours in medium supplemented with 10% FCS with $1\times10^{-5}$ M Bix-01294 as indicated. For ChIP and ChIP-seq, cells were cultivated for 210 min with or without DHT $10^{-7}$ M and 6 hours for expression analysis. Cells were cultivated for 3 days (FIG. 4f, g) with DHT $10^{-6}$ M as indicated.

Chromosome Conformation Capture (3C):

3C was essentially performed as previously described[40]. LNCaP cells were grown for 72 hours in medium supplemented with 10% double-stripped FCS, treated for 210 min with or without DHT $10^{-7}$ M, washed in PBS, and trypsinized 2 min at 37° C. After washing, cells were resuspended in PBS, filtered through a 40 μm cell strainer and collected in an ice cold 2% formaldehyde solution. After 15 min incubation at 4° C., fixation was stopped by adding glycine and cells were pelleted. After washing, cells were resuspended in nuclear isolation buffer (10 mM HEPES-KOH pH 7.9, 1.5 mM MgCl2, 10 mM KCl, 0.5 mM DTT, Complete protease inhibitor cocktail, Roche), allowed to swell on ice for 10 min, vortexed for 10 seconds at low speed, and pelleted. Isolated nuclei were resuspended in NEB restriction buffer, SDS was added to a final concentration of 0.5%, and nuclei were incubated for 1 h at 37° C. while shaking. Upon addition of Triton X-100, samples were incubated for 1 h at 37° C. to sequester SDS. 50 μl of the sample were taken and used as an undigested control. 600 U restriction enzyme were added and samples were incubated overnight at 37° C. while shaking. 40 μl 20% SDS solution was added and incubated for 20 min at 65° C. to inactivate the restriction enzyme. Then, 6.2 ml ligation buffer without ATP and 375 μl Triton X-100 were added and incubated for 1 h at 37° C. 60 μl of 100 μM ATP solution and 2000 U T4 DNA Ligase were added. Following incubation for 4 h at 16° C. and 30 min at RT, Proteinase K was added and reversal of cross-Links was performed by overnight incubation at 65° C. Upon digestion with RNAse A, DNA was isolated by phenol-chloroform extraction followed by a purification step with QIAgen PCR purification kit. Purified DNA samples were analyzed on a Roche LightCycler®480 by TaqMan-based qPCR. The TaqMan primers and probe for Enhancer-Breakpoint were: FW: 5'-GAGCCATGAAAGTCTTTGC-TATGA-3' (SEQ ID NO: 9), probe 5'-AAGTTCACACCTTCCTGGGT-3' (SEQ ID NO:10), RV: 5'-GTGATCCTTCCCACCTGTACATT-3' (SEQ ID NO:11). The PCR master mix was prepared as follows: 10 μl Fast universal Master mix (Life Technologies), 7 μl H2O, 1 μl TaqMan primers and probe and 300 ng DNA template. To verify Enhancer-Breakpoint PCR product, samples were analyzed on a 2% agarose gel and sequenced. Nomalization was done against the product obtained for Ctrl corresponding to a genomic DNA region amplified by following primers: 5'-AGGACACAGGAAAGCGATGG-3' (SEQ ID NO:12) and 5'-AGAGGGCTGTCTTGATTCGC-3' (SEQ ID NO:13).

Fluorescence In-Situ Hybridization (FISH):

To determine TMPRSS2-ERG fusion status in LNCaP cells, a FISH break-apart assay was performed as described previously[41]. The FISH probe consists of two BAC clones spanning the centromeric and telomeric region of the ERG locus on chromosome 21q22.2: RP11-24A11 labelled with biotin-14-dCTP (red) and RP11-137J13 labelled with digoxigenin-dUTP (green). After harvesting, LNCaP cells were incubated with 0.075 M KCl at 37° C. for 15 min and fixed on slides (acetic acid/methanol 1:3). Slides were pre-treated with 2×SSC at 37° C. for 60 min, digested with 1:25 Digest-A11 III at 37° C. for 6 min and dehydrated in an ascending ethanol series. The probes were denatured at 73° C. for 5 min and subsequently co-denaturized with the cells (85° C., 4 min). Hybridization of the two probes was performed at 37° C. overnight. Post hybridisation washing was done with 0.5×SSC at 75° C. for 5 min and the fluorescence detection was carried out using streptavidin-Alexa-594 and FITC-anti-DIG conjugates (dilution 1:250).

Finally slides were counterstained with DAPI and mounted and independently evaluated by two persons.

Data Analysis:

Data are represented as mean+standard error of the mean (SEM). Significance was calculated by a two-tailed Student's t test.

REFERENCES

1: Baca, S. C. et al. Punctuated evolution of prostate cancer genomes. Cell 153, 666-677 (2013).
2: Tomlins, S. A. et al. Recurrent fusion of TMPRSS2 and ETS transcription factor genes in prostate cancer. Science 310, 644-648 (2005).
3: Lin, C. et al. Nuclear receptor-induced chromosomal proximity and DNA breaks underlie specific translocations in cancer. Cell 139, 1069-1083 (2009).
4: Haffner, M. C. et al. Androgen-induced TOP2B-mediated double-strand breaks and prostate cancer gene rearrangements. Nat. Genet. 42, 668-675 (2010).
5: Siegel, R., Naishadham, D. & Jemal, A. Cancer statistics, 2013. C.A. Cancer J. Clin. 63, 11-30 (2013).
6: Taylor, B. S. et al. Integrative genomic profiling of human prostate cancer. Cancer Cell 18, 11-22 (2010).
7: Rubin, M. A., Maher, C. A. & Chinnaiyan, A. M. Common gene rearrangements in prostate cancer. J. Clin. Oncol. 29, 3659-3668 (2011).
8: Barbieri, C. E. et al. Exome sequencing identifies recurrent SPOP, FOXA1 and MED12 mutations in prostate cancer. Nat. Genet. 44, 685-689 (2012).
9: Burkhardt, L. et al. CHD1 is a 5q21 tumor suppressor required for ERG rearrangement in prostate cancer. Cancer Res. 73, 2795-2805 (2013).
10: Metzger, E. et al. LSD1 demethylates repressive histone marks to promote androgen-receptor-dependent transcription. Nature 437, 436-439 (2005).
11: Kahl, P. et al. Androgen receptor coactivators lysine-specific histone demethylase 1 and four and a half LIM domain protein 2 predict risk of prostate cancer recurrence. Cancer Res. 66, 11341-11347(2006).
12: Cai, C. et al. Androgen receptor gene expression in prostate cancer is directly suppressed by the androgen receptor through recruitment of lysine-specific demethylase 1. Cancer Cell 20, 457-471 (2011).
13: Shi, Y. et al. Histone demethylation mediated by the nuclear amine oxidase homolog LSD1. Cell 119, 941-953. (2004).
14: Kim, J. et al. Tudor, MBT and chromo domains gauge the degree of lysine methylation. EMBO Rep. 7, 397-403 (2006).
15: Flanagan, J. F. et al. Double chromodomains cooperate to recognize the methylated histone H3 tail. Nature 438, 1181-1185 (2005).
16: Tan, P. Y. et al. Integration of regulatory networks by NKX3-1 promotes androgen-dependent prostate cancer survival. Mol. Cell. Biol. 32, 399-414 (2012).
17: Kubicek, S. et al. Reversal of H3K9me2 by a small-molecule inhibitor for the G9a histone methyltransferase. Mol. Cell 25, 473-481 (2007).
18: Wang, Q., Carroll, J. S. & Brown, M. Spatial and temporal recruitment of androgen receptor and its coactivators involves chromosomal looping and polymerase tracking. Mol. Cell 19, 631-642 (2005).
19: Metzger, E. et al. Phosphorylation of histone H3T6 by PKCbeta(I) controls demethylation at histone H3K4. Nature 464, 792-796 (2010).
20: Lee, D. Y., Northrop, J. P., Kuo, M. H. & Stallcup, M. R. Histone H3 lysine 9 methyltransferase G9a is a transcriptional coactivator for nuclear receptors. J. Biol. Chem. 281, 8476-8485 (2006).
21: Huang, S. et al. Recurrent deletion of CHD1 in prostate cancer with relevance to cell invasiveness. Oncogene 31, 4164-4170 (2012).
22: Langmead, B., Trapnell, C., Pop, M. & Salzberg, S. L. Ultrafast and memory-efficient alignment of short DNA sequences to the human genome. Genome Biol. 10, R25 (2009).
23: Zhang, Y. et al. Model-based analysis of ChIP-Seq (MACS). Genome Biol. 9, R137 (2008).
24: Thorvaldsdottir, H., Robinson, J. T. & Mesirov, J. P. Integrative Genomics Viewer (IGV): high-performance genomics data visualization and exploration. Brief Bioinform. 14, 178-192 (2013).
25: Heinz, S. et al. Simple combinations of lineage-determining transcription factors prime cis-regulatory elements required for macrophage and B cell identities. Mol. Cell 38, 576-589 (2010).
26: Keller, S. et al. High-precision isothermal titration calorimetry with automated peak-shape analysis. Anal Chem. 84, 5066-5073 (2012).
27: Schuck, P. Size-distribution analysis of macromolecules by sedimentation velocity ultracentrifugation and 1 amm equation modeling. Biophys. J. 78, 1606-1619 (2000).
28: Kabsch, W. XDS. Acta Crystallogr. D. Biol. Crystallogr. 66, 125-132 (2010).
29: Evans, P. R. & Murshudov, G. N. How good are my data and what is the resolution? Acta Crystallogr. D. Biol. Crystallogr. 69, 1204-1214 (2013).
30: McCoy, A. J. et al. Phaser crystallographic software. J. Appl. Crystallogr. 40, 658-674 (2007).
31: Emsley, P., Lohkamp, B., Scott, W. G. & Cowtan, K. Features and development of Coot. Acta Crystallogr. D. Biol. Crystallogr. 66, 486-501 (2010).
32: Murshudov, G. N., Vagin, A. A. & Dodson, E. J. Refinement of macromolecular structures by the maximum-likelihood method. Acta. Crystallogr. D. Biol. Crystallogr. 53, 240-255 (1997).
33: The CCP4 suite: programs for protein crystallography. Acta Crystallogr. D. Biol. Crystallogr. 50, 760-763 (1994).
34: Trapnell, C. et al. Differential gene and transcript expression analysis of RNA-seq experiments with TopHat and Cufflinks. Nat. Protoc. 7, 562-578 (2012).
35: Robinson, M. D. & Smyth, G. K. Small-sample estimation of negative binomial dispersion, with applications to SAGE data. Biostatistics 9, 321-332 (2008).
36: Anders, S. & Huber, W. Differential expression analysis for sequence count data. Genome Biol. 11, R106 (2010).
37: Dengjel, J. et al. Identification of autophagosome-associated proteins and regulators by quantitative proteomic analysis and genetic screens. Mol. Cell. Proteomics 11, M111 014035 (2012).
38: Cox, J. & Mann, M. MaxQuant enables high peptide identification rates, individualized p.p.b.-range mass accuracies and proteome-wide protein quantification. Nat. Biotechnol. 26, 1367-1372 (2008).
39: Cox, J. et al. Andromeda: a peptide search engine integrated into the MaxQuant environment. J. Proteome Res. 10, 1794-1805 (2011).
40: Hagege, H. et al. Quantitative analysis of chromosome conformation capture assays (3C-qPCR). Nat. Protoc. 2, 1722-1733 (2007).

41: Perner, S. et al. TMPRSS2:ERG fusion-associated deletions provide insight into the heterogeneity of prostate cancer. Cancer Res. 66, 8337-8341 (2006).

REFERENCES FOR SUPPLEMENTARY TABLE 1

41: Weiss, M. & Hilgenfeld, R. On the use of the merging R factor as a quality indicator for X-ray data. J. Appl. Crystallogr. 30, 203-205 (1997).

42: Karplus, P. A. & Diederichs, K. Linking Crystallographic Model and Data Quality. Science 336, 1030-1033 (2012).

43: Cruickshank, D. W. J. Remarks about protein structure precision. Acta Crystallographica D55, 583-601 (1999).

44: Brlinger, A. T. Free R value: a novel statistical quantity for assessing the accuracy of crystal structures. Nature 355, 472-475 (1992).

The invention claimed is:

1. A method of screening for a compound inhibiting the interaction between lysine-specific demethylase 1 modified at lysine residue 114 by two methyl-groups (LSD1me2) and chromodomain-helicase-DNA-binding protein 1 (CHD1) comprising the steps of:
   1) Contacting a compound with CHD1 or a fragment thereof;
   2) Determining whether said compound binds to CHD1 or a fragment thereof at the binding site for LSD1me2;
   wherein a compound inhibiting the interaction between LSD1me2 and CHD1 binds to CHD1 at the binding site for LSD1me2, and wherein said fragment of CHD1 comprises chromodomain 1 and chromodomain 2 of CHD1.

2. The method according to claim 1, wherein a fragment of CHD1 is used.

3. The method according to claim 1, wherein said binding site for LSD1me2 in CHD1 is defined by amino acids Y295, W322, W325 from chromodomain 1 and D408 and D425 from chromodomain 2 of CHD1.

4. The method according to claim 1, wherein said binding site for LSD1me2 in CHD1 is defined by amino acid D425 of CHD1.

5. The method according to claim 1, wherein said determining step 2) is carried out by a method selected from the group consisting of nuclear magnetic resonance spectroscopy, mass spectrometry, infrared spectroscopy, Raman spectroscopy, electron microscopy, X-ray crystallography and combinations thereof.

* * * * *